US011193937B2

(12) United States Patent
Dolled-Filhart et al.

(10) Patent No.: US 11,193,937 B2
(45) Date of Patent: Dec. 7, 2021

(54) IMMUNOHISTOCHEMICAL ASSAY FOR DETECTING EXPRESSION OF PROGRAMMED DEATH LIGAND 1 (PD-L1) IN TUMOR TISSUE

(71) Applicant: Merck Sharp & Dohme Corp., Rahway, NJ (US)

(72) Inventors: Marisa Dolled-Filhart, Highland Park, NJ (US); Kenneth Emancipator, Bernardsville, NJ (US); Frank Lynch, Newtown, PA (US); Robert H. Pierce, San Francisco, CA (US); Dianna Wu, Skillman, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 84 days.

(21) Appl. No.: 15/712,246

(22) Filed: Sep. 22, 2017

(65) Prior Publication Data

US 2018/0080938 A1 Mar. 22, 2018

Related U.S. Application Data

(63) Continuation of application No. 14/782,067, filed as application No. PCT/US2014/032305 on Mar. 31, 2014, now abandoned.

(60) Provisional application No. 61/807,581, filed on Apr. 2, 2013.

(51) Int. Cl.
*G01N 33/574* (2006.01)
*A61K 39/00* (2006.01)

(52) U.S. Cl.
CPC ... *G01N 33/57492* (2013.01); *G01N 33/5743* (2013.01); *G01N 33/57415* (2013.01); *G01N 33/57423* (2013.01); *G01N 2333/70596* (2013.01); *G01N 2800/52* (2013.01)

(58) Field of Classification Search
CPC ....... G01N 33/57492; G01N 33/57415; G01N 33/57423; G01N 33/5743; G01N 2333/70596; G01N 2800/52
See application file for complete search history.

(56) References Cited

U.S. PATENT DOCUMENTS

| 9,709,568 B2 | 7/2017 | Pierce et al. | |
| 2009/0215090 A1* | 8/2009 | Fouret | C07K 16/40 435/7.23 |
| 2010/0266617 A1* | 10/2010 | Carven | C07K 16/2818 424/172.1 |
| 2012/0251537 A1 | 10/2012 | Ahmed et al. | |
| 2013/0064882 A1 | 3/2013 | Russo et al. | |

FOREIGN PATENT DOCUMENTS

| WO | 2007082154 A2 | 7/2007 |
| WO | 2008156712 A1 | 12/2008 |
| WO | WO2010132958 A1 | 11/2010 |
| WO | 2013173223 A1 | 11/2013 |
| WO | 2014100079 A1 | 6/2014 |
| WO | WO2014100079 | * 6/2014 |

OTHER PUBLICATIONS

Mu et al (Med Oncol 28:682-688, 2011 (Year: 2011).*
Abbott, et al., "Binding to human dipeptidyl IV by adenosine deaminase and antibodies . . . ", Eur J Biochem, 1999, pp. 798-810, vol. 266.
Allred, et al., "Prognostic and predictive factors in breast cancer by immunohistochemical analysis", Mod Pathol., 1998, pp. 798-810, vol. 266.
Brahmer, et al., "Phase I study of single-agent anti-programmed death-1 (MDX-1106) in refractory solid tumors . . . ", Journal Clinical Oncology, 2010, pp. 3167, vol. 28.
Bremnes et al., "The Role of Tumor Stroma in Cancer Progression and Prognosis", J. Thor, Oncol, 2011, pp. 209-217, vol. 6.
Gadiot et al., "Overall Survival and PD-L1 Expression in Metastasized Malignant Melanoma", Cancer, 2011, 2192-2201, vol. 117.
Gao et al., "Overexpression of PD-L1 Significantly Associates with Tumor Aggressiveness and Postoperative Recurrence in Human Hepatocellular Carcinoma":, Clinical Cancer Research, 2009, 971-979, vol. 15.
Ghebeh et al., "The B7-H1 (PD-L1) T Lymphocyte-Inhibitory Molecule Is Expressed in Breast Cancer Patients with Infiltrating Ductal Carcinoma: Correlation with Important High-Risk Prognostic Factors", Neoplasia, 2006, 190-198, vol. 8.
Hamanishi et al., "Programmed cell death 1 ligand 1 and tumor-infiltrating CD8+ T lymphocytes are prognostic factors of human ovarian cancer", Proceedings of the National Academy of Sciences USA, 2007, 3360-3365, vol. 104.
International Search Report of PCT/US14/032305, dated Sep. 10, 2014.
Iwai, "Involvement of PD-L1 on tumor cells in the escape from host immune system and tumor immunotherapy by PD-L1 blockade", Proc. Natl. Acad Sci., 2002, 12293-12297, vol. 99.
Mccarty Jr., et al., "Use of a monoclonal anti-estrogen receptor antibodyin the immunohistochemical evaluation of human tumors", Cancer Research, 1986, 4244s-4248s, vol. 46 (Supp 8).
Mu, et al., "High expression of PD-L1 in lung cancer may contribute to poor High expression of PD-L1 in lung cancer may contribute to poor tumor infiltrating dendritic cells maturation", Medical Oncology, 2011, pp. 682-688, vol. 28.
Ohigashi, et al., "Clinical Significance of Programmed Death-1 Ligand-1 and Programmed Death-1 Ligand-2 Expression in Human Esophageal Cancer", Clinical Cancer Research, 2005, 2947-2953, vol. 11.

(Continued)

*Primary Examiner* — Lei Yao
(74) *Attorney, Agent, or Firm* — Andrew W. Custer; Anna L. Cocuzzo

(57) ABSTRACT

The present disclosure provides processes for describing and quantifying the expression of human programmed death ligand-1 (PD-L1) in tumor tissue sections as detected by immunohistochemical assay using an antibody that specifically binds to PD-L1. The results generated using these processes have a variety of experimental, diagnostic and prognostic applications.

4 Claims, 11 Drawing Sheets

Specification includes a Sequence Listing.

(56) References Cited

OTHER PUBLICATIONS

Detre, et al., "A "quickscore" method for immunohistochemical semiquantitation: validation for oestorgen receptor in breast carcimomas", Journal of Clinical Pathology, 1995, pp. 876-878, vol. 48, No. 9.

Sun, et al., "PD L1 expression analysis in gastric carcinoma tissue and blocking of tumor-associated PD-L1 signaling by two functional monoclonal antibodies", Tissue Antigens, 2007, pp. 19-27, vol. 69.

Sznol, et al., "Antagonist Antibodies to PD-1 and B7-Hi (PD-L1) in the Treatment of Advanced Human Cancer", Clinical Cancer Research, 2013, pp. 1021-1034, vol. 19.

Taube, et al.,"Colocalization of inflammatory response with B7-H1 expression in human melanocytic lesions supports an adaptive resistance mechanism of immune escape", Sci. Transl. Med., 2012, pp. 127ra37, vol. 4.

Thompson, et al., "Costimulatory B7-H1 in renal cell carcinoma patients: Indicator of tumor aggressiveness and potential therapeutic target", PNAS, 2004, 17174-17179, vol. 101(49).

Thompson et al., "Tumor B7-H1 Is Associated with Poor Prognosis in Renal Cell Carcinoma Patients with Long-Term Follow-up", Cancer Research, 2006, 3381-3385, vol. 66.

Topalian, et al., "Safety, Activity, and Immune Correlates of Anti-PD-1 Antibody in Cancer", New England Journal of Medicine, 2012, 2443-2454, vol. 366(26).

Topalian, et al., "Anti-PD-1 (BMS-936558, MDX-1106) in patients with advanced solid tumors: Clinical activity, safety and a potential biomarker for response", 2012 ASCO Annual Meeting, Jun. 21, 2012, XP055301753.

Written Opinion of PCT/US14/032305 dated Sep. 10, 2014.

Yang et al., "PD-L1: PD-1 Interaction Contributes to the Functional Suppression of T-Cell Responses to Human Uveal Melanoma Cells In Vitro", Investigative Ophthalmology & Visual Science, 2008, 2518-2525, vol. 49(6).

Zhang, et al., "PD-1/PD-L1 interactions inhibit antitumor innune responses in a murine acute myeloid leukemia model", Blood, 2009, pp. 1545-1552, vol. 114, No. 8.

U.S. Appl. No. 14/782,067, filed Oct. 2, 2015,

Brahmer et al., Safety and Activity of Anti-PD-L1 Antibody in Patients with Advanced Cancer, The New England Journal of Medicine, 2012, pp. 2455-2465, vol. 366, No. 26.

Dong et al., Tumor-associated B7-H1 promotes T-cell apoptosis: A potential mechanism of immune evasion, Nature Medicine, 2002, pp. 793-800, vol. 8(8).

Huang, C., Clinical application of biological markers for treatrments of resectable non-small-cell lung cancers, British Journal of Cancer, 2005, 1231-1239, 92.

Kirkegaard, T., Observer variation in immunohistochemical analysis of protein expression, time for a change?, Histopathology, 2006, 787-794, 48.

Patnaik, Amita, Phase I Study of Pembrolizumab (MK-3475, Anti-PD-1 Monoclonal Antibody) in Patients with Advanced Solid Tumors, Clinical Cancer Research, 2015, 4286-4293, 21(19).

Rosenblatt, Jacalyn, PD-1 blockade by CT-011, anti PD-1 antibody, enhances ex-vivo T cell responses to autologous dendritic/myeloma fusion vaccine, Journal of Immunotherapy, 2011, 409-418, 34(5).

Strome et al., B7-H1 Blockade Augments Adoptive T-Cell Immunotherapy for Squamous Cell Cancinoma, Cancer Research, 2003, pp. 6501-6505, vol. 63.

Zitvogel, Laurence, Targeting PD-1/PD-L1 interactions for cancer immunotherapy, Oncolmmunology, 2012, 1223-1225, 1:8.

\* cited by examiner

Heavy chain

[ATGGAAAGGCACTGGATCTTTCTCTTCCTGTTTTCAGTAACTGCAGGTGTCCACTCC]

CAGGTCCAGGTTCAGCAGTCTGGGGCTGAACTGGCAGAACCTGGGGCCTCAGTGAAGATGTCCT
GCAAGGCCTCTGGCTACATCTTTACTAGCTACTGGATGCACTGGCTAAAGCAGAGGCCTGGACA
GGGTCTGGAATGGATTGGATACATTAATCCCAGCAGTGATTATAATGAATACAGTGAGAAATTC
ATGGACAAGGCCACATTGACTGCAGACAAAGCCTCCACCACAGCCTACATGCAACTGATCAGCC
TGACATCTGAGGACTCTGCAGTCTATTACTGTGCAAGATCGGGATGGTTAGTACATGGAGACTA
TTATTTTGACTACTGGGGCCAAGGCACCACTCTCACAGTCTCCTCA

[M E R H W I F L F L F S V T A G V H S]
Q V Q V Q Q S G A E L A E P G A S V K M S C K A S G Y I F T S Y
W M H W L K Q R P G Q G L E W I G Y I N P S S D Y N E Y S E K F
M D K A T L T A D K A S T T A Y M Q L I S L T S E D S A V Y Y C
A R S G W L V H G D Y Y F D Y W G Q G T T L T V S S

Light chain

[ATGGATTCACAGGCCCAGGTTCTTATATTGCTGCTGCTATGGGTATCTGGTACCTTTGGG]

GACATTGTGATGTCACAATCTCCATCCTCCCTGGCTGTGTCAGCAGGAGAGAAGGTCACTATGA
GCTGCAAATCCAGTCAGAGTCTGCTCAACAGTAGAACCCGAAAGAACTACTTGGCTTGGTACCA
GCAGAAACCAGGGCAGTCTCCTAAACTGCTGATCTACTGGGCATCCACTAGGGAATCTGGGGTC
CCTGATCGCTTCACAGGCAGTGGATCTGGGACAGATTTCACTCTCACCATCAGCAGTGTGCAGG
CTGAAGACCTGGCAGTTTATTACTGCCAGCAATCTTATGATGTGGTCACGTTCGGTGCTGGGAC
CAAGCTGGAGCTGAAA

Heavy chain

[ATGGAAAGGCACTGGATCTTTCTCTTCCTGTTTTCAGTAACTGCAGGTGTCCACTCC]

CAGGTCCACCTTCAGCAGTCTGGGGCTGAACTGGCAAAACCTGGGGCCTCAGTGAAGATGTCCT
GCAAGGCTTCTGGCTACACGTTTACTAGTTACTGGATACACTGGATAAAGCAGAGGCCTGGACA
GGGTCTGGAATGGATTGGATACATTAATCCTTCCTCTGGTTATCATGAATACAATCAGAAATTC
ATTGACAAGGCCACATTGACTGCTGACAGATCCTCCAGCACAGCCTACATGCACCTGACCAGCC
TGACGTCTGAAGACTCTGCAGTCTATTACTGTGCAAGATCGGGATGGTTAATACATGGAGACTA
CTACTTTGACTTCTGGGGCCAAGGCACCACTCTCACAGTCTCCTCA

[M E R H W I F L F L F S V T A G V H S]
Q V H L Q Q S G A E L A K P G A S V K M S C K A S G Y T F T <u>S Y</u>
<u>W I H</u> W I K Q R P G Q G L E W I G <u>Y I N P S S G Y H E Y N Q K F</u>
<u>I D</u> K A T L T A D R S S S T A Y M H L T S L T S E D S A V Y Y C
A R <u>S G W L I H G D Y Y F D F</u> W G Q G T T L T V S S

Light chain

[ATGGATTCACAGGCCCAGGTTCTTATATTGCTGCTGCTATGGGTATCTGGTACCTGTGGG]

GACATTGTGATGTCACAGTCTCCCTCCTCCCTGGCTGTGTCAGCAGGAGAGAAGGTCACTATGA
CCTGCAAATCCAGTCAGAGTCTGCTCCACACTAGCACCCGAAAGAACTACTTGGCTTGGTACCA
GCAGAAACCAGGGCAGTCTCCTAAACTGCTGATCTATTGGGCATCCACTAGGGAATCTGGGGTC
CCTGATCGCTTCACAGGCAGTGGATCTGGGACAGATTTCACTCTCACCATCAGCAGTGTGCAGG
CTGAAGACCTGGCAGTTTATTACTGCAAACAATCTTATGATGTGGTCACGTTCGGTGCTGGGAC
CAAGCTGGAGCTGAAA

Gln Val Gln Leu Val Gln Ser Gly Val Glu Val Lys Lys Pro Gly Ala
Ser Val Lys Val Ser Cys Lys Ala Ser Gly Tyr Thr Phe Thr Asn Tyr
Tyr Met Tyr Trp Val Arg Gln Ala Pro Gly Gln Gly Leu Glu Trp Met
Gly Gly Ile Asn Pro Ser Asn Gly Gly Thr Asn Phe Asn Glu Lys Phe
Lys Asn Arg Val Thr Leu Thr Thr Asp Ser Ser Thr Thr Thr Ala Tyr
Met Glu Leu Lys Ser Leu Gln Phe Asp Asp Thr Ala Val Tyr Tyr Cys
Ala Arg Arg Asp Tyr Arg Phe Asp Met Gly Phe Asp Tyr Trp Gly Gln
Gly Thr Thr Val Thr Val Ser Ser Ala Ser Thr Lys Gly Pro Ser Val
Phe Pro Leu Ala Pro Cys Ser Arg Ser Thr Ser Glu Ser Thr Ala Ala
Leu Gly Cys Leu Val Lys Asp Tyr Phe Pro Glu Pro Val Thr Val Ser
Trp Asn Ser Gly Ala Leu Thr Ser Gly Val His Thr Phe Pro Ala Val
Leu Gln Ser Ser Gly Leu Tyr Ser Leu Ser Ser Val Val Thr Val Pro
Ser Ser Ser Leu Gly Thr Lys Thr Tyr Thr Cys Asn Val Asp His Lys
Pro Ser Asn Thr Lys Val Asp Lys Arg Val Glu Ser Lys Tyr Gly Pro
Pro Cys Pro Pro Cys Pro Ala Pro Glu Phe Leu Gly Gly Pro Ser Val
Phe Leu Phe Pro Pro Lys Pro Lys Asp Thr Leu Met Ile Ser Arg Thr
Pro Glu Val Thr Cys Val Val Val Asp Val Ser Gln Glu Asp Pro Glu
Val Gln Phe Asn Trp Tyr Val Asp Gly Val Glu Val His Asn Ala Lys
Thr Lys Pro Arg Glu Glu Gln Phe Asn Ser Thr Tyr Arg Val Val Ser
Val Leu Thr Val Leu His Gln Asp Trp Leu Asn Gly Lys Glu Tyr Lys
Cys Lys Val Ser Asn Lys Gly Leu Pro Ser Ser Ile Glu Lys Thr Ile
Ser Lys Ala Lys Gly Gln Pro Arg Glu Pro Gln Val Tyr Thr Leu Pro
Pro Ser Gln Glu Glu Met Thr Lys Asn Gln Val Ser Leu Thr Cys Leu
Val Lys Gly Phe Tyr Pro Ser Asp Ile Ala Val Glu Trp Glu Ser Asn

FIG.9A

Gly Gln Pro Glu Asn Asn Tyr Lys Thr Thr Pro Pro Val Leu Asp Ser
Asp Gly Ser Phe Phe Leu Tyr Ser Arg Leu Thr Val Asp Lys Ser Arg
Trp Gln Glu Gly Asn Val Phe Ser Cys Ser Val Met His Glu Ala Leu
His Asn His Tyr Thr Gln Lys Ser Leu Ser Leu Ser Leu Gly Lys

FIG.9B

Glu Ile Val Leu Thr Gln Ser Pro Ala Thr Leu Ser Leu Ser Pro Gly
Glu Arg Ala Thr Leu Ser Cys Arg Ala Ser Lys Gly Val Ser Thr Ser
Gly Tyr Ser Tyr Leu His Trp Tyr Gln Gln Lys Pro Gly Gln Ala Pro
Arg Leu Leu Ile Tyr Leu Ala Ser Tyr Leu Glu Ser Gly Val Pro Ala
Arg Phe Ser Gly Ser Gly Ser Gly Thr Asp Phe Thr Leu Thr Ile Ser
Ser Leu Glu Pro Glu Asp Phe Ala Val Tyr Tyr Cys Gln His Ser Arg
Asp Leu Pro Leu Thr Phe Gly Gly Gly Thr Lys Val Glu Ile Lys Arg
Thr Val Ala Ala Pro Ser Val Phe Ile Phe Pro Pro Ser Asp Glu Gln
Leu Lys Ser Gly Thr Ala Ser Val Val Cys Leu Leu Asn Asn Phe Tyr
Pro Arg Glu Ala Lys Val Gln Trp Lys Val Asp Asn Ala Leu Gln Ser
Gly Asn Ser Gln Glu Ser Val Thr Glu Gln Asp Ser Lys Asp Ser Thr
Tyr Ser Leu Ser Ser Thr Leu Thr Leu Ser Lys Ala Asp Tyr Glu Lys
His Lys Val Tyr Ala Cys Glu Val Thr His Gln Gly Leu Ser Ser Pro
Val Thr Lys Ser Phe Asn Arg Gly Glu Cys

FIG.10

IMMUNOHISTOCHEMICAL ASSAY FOR DETECTING EXPRESSION OF PROGRAMMED DEATH LIGAND 1 (PD-L1) IN TUMOR TISSUE

CROSS-REFERENCE TO RELATED APPLICATIONS

This application is a continuation application of U.S. application Ser. No. 14/782,067, filed Oct. 2, 2015, now abandoned, which is a § 371 National Stage Application of PCT/US2014/32305, international filing date of Mar. 31, 2014, which claims the benefit of U.S. Provisional Application Ser. No. 61/807,581, filed Apr. 2, 2013.

FIELD OF THE INVENTION

The present invention relates to the quantitation of PD-L1 expression in animal tissue samples by immunohistochemical (IHC) assay. The invention also relates to the identification of PD-L1 expression levels that correlate with response of cancer patients to therapy with antagonists of Programmed Death 1 (PD-1).

BACKGROUND OF THE INVENTION

PD-L1 is a cell surface glycoprotein that is one of two known ligands for Programmed Death 1 (PD-1), which is recognized as an important player in immune regulation and the maintenance of peripheral tolerance. Expression of PD-L1 has been observed on the surface of a variety of immune cells, including naive lymphocytes and activated B and T cells, monocytes and dendritic cells (Id.). Furthermore, PD-L1 mRNA is expressed by non-lymphoid tissues including vascular endothelial cells, epithelial cells, muscle cells, and in tonsil and placental tissue. See, e.g., Keir, M. E. et al., *Annu Rev Immunol.* 26:677-704 (2008); Sharp A. H. et al., *Nature Immunol.* 8:239-245 (2007); Okazaki T and Honjo T, *Internat. immunol.* 19:813-824 (2007).

PD-L1 expression has also been observed in a variety of human cancers, and interaction of tumor-cell expressed PD-L1 with PD-1 can induce inhibition or apoptosis of tumor-specific T cells. In large sample sets of e.g. ovarian, renal, colorectal, pancreatic, liver cancers and melanoma it was shown that PD-L1 expression correlated with poor prognosis and reduced overall survival irrespective of subsequent treatment. Anti-PD-1 monoclonal antibodies (mAbs) that block binding of PD-L1 to PD-1 have been shown to have anti-tumor activity against a variety of tumor types, with early human clinical data suggesting that patients whose tumors express PD-L1 are more likely to respond to anti-PD-1 therapy. See, e.g., Iwai et al., *PNAS* 99:12293-12297 (2002); Ohigashi et al., *Clin Cancer Res* 11:2947-2953 (2005); Ghebeh et al., *Neoplasia* 8:190-198 (2006); Hamanishi, J et al., *PNAS* 104:3360-3365 (2007); Yang et al., *Invest Ophthalmol Vis Sci.* 49(6):2518-2525 (2008); Gao et al., *Clin Cancer Res* 15:971-979 (2009); Brahmer J. R. et al., *J Clin Oncol.* 28:3167-3175 (2010).

Published studies of PD-L1 expression in human tumors have generally been based on immunohistochemistry (IHC) analysis of frozen or formalin-fixed, paraffin-embedded (FFPE) tumor tissue sections stained with a primary antibody that binds to PD-L1. See, e.g., Thompson, R. H., et al., *PNAS* 101 (49); 17174-17179 (2004); Thompson, R. H. et al., *Cancer Res.* 66:3381-3385 (2006); Gadiot, J., et al., *Cancer* 117:2192-2201 (2011); Taube, J. M. et al., *Sci Transl Med* 4, 127ra37 (2012); and Toplian, S. L. et al., *New Eng. J Med.* 366 (26): 2443-2454 (2012). These studies described several approaches for quantifying PD-L1 expression in IHC assays of tumor tissue sections.

One approach employed a simple binary end-point of positive or negative for PD-L1 expression, with a positive result defined in terms of the percentage of tumor cells that exhibited histologic evidence of cell-surface membrane staining. The minimum threshold of membrane-stained tumor cells selected as the cut-off point at which a tumor tissue section was counted as positive for PD-L1 expression was either 1% of total tumor cells (Gadiot et al.) or 5% (Toplian et al., supra,) of total tumor cells.

In another approach, PD-L1 expression in the tumor tissue section was quantified in the tumor cells as well as in infiltrating immune cells, which predominantly comprise lymphocytes (Taube et al., supra; Thompson). The percentage of tumor cells and infiltrating immune cells that exhibited membrane staining were separately quantified as <5%, 5 to 9%, and then in 10% increments up to 100%. For tumor cells, PD-L1 expression was counted as negative if the score was <5% score and positive if the score was ≥5%. PD-L1 expression in the immune infiltrate was reported as a semi-quantitative measurement called the adjusted inflammation score (AIS), which is determined by multiplying the percent of membrane staining cells by the intensity of the infiltrate, which was graded as none (0), mild (score of 1, rare lymphocytes), moderate (score of 2, focal infiltration of tumor by lymphohistiocytic aggregates), or severe (score of 3, diffuse infiltration). A tumor tissue section was counted as positive for PD-L1 expression by immune infiltrates if the AIS was ≥5.

Diagnostic pathologists have devised other objective criteria for assigning a semi-quantitative score to the observed expression level of a target protein detected in IHC assays, including a three-to four-point scale, an HSCORE (McCarty, K. S. Jr, et al., *Cancer Res.* 46(suppl 8):42445-42485 (1986) and the criteria of Allred et al. (Allred D C, Harvey J M, Berardo M, Clark G M. *Mod Pathol.* 11:155-168 (1998). A 4-point HSCORE (McCarty et al) was calculated based on (a) intensity of staining ranging from 0 (no staining), 1+ (weak staining), 2+ (distinct staining), 3+ (strong staining) and 4+ (stained cells have minimal light transmission through them, meaning extremely strong/saturated signal) and multiplying by the percent of cells staining at each intensity (0 to 100%). Allred scoring (Allred et al) is based on calculating a Total Score (TS, range 0 to 8) by adding together a proportion score (PS) and an intensity score (IS). PS is the proportion of positive tumor cells ranging from 0 to 5 (0=no positive cells, 1=1/100 cells are positive, 2=1/10 cells are positive, 3=1/3 cells are positive, 4=2/3 of cells are positive, 5=all tumor cells are positive). IS means the average staining intensity of positive tumor cells ranging from 0 to 3 (0=negative, 1=weak, 2=intermediate staining, 3=strong staining).

However, as described herein, the inventors discovered that due to the complexity of staining patterns observed in various tumor tissue sections stained with an anti-PD-L1 antibody, new scoring rules are needed to accurately and reliably quantify the level of PD-L1 expression across multiple tissue samples and pathologists doing the scoring.

SUMMARY OF THE INVENTION

The inventors have surprisingly discovered that quantifying PD-L1 expression using IHC analysis, beyond a simple binary positive/negative characterization, can provide valuable predictive information to identify patients who are more likely to respond to treatment with anti-PD-1 therapy. Furthermore, the inventors have identified a unique scoring process that is intended to facilitate standardizing the quantitation of PD-L1 expression across multiple stained tissue sections and pathology laboratories. A PD-L1 expression score produced by performing this scoring process may be useful in selecting patients to receive anti-PD-1 therapy.

Thus, in one aspect, the present invention provides a novel process for scoring the expression of a PD-L1 protein in a tumor sample removed from an animal. The process comprises obtaining a tissue section from the tumor that has been stained with an antibody that binds to the PD-L1 protein (anti-PD-L1 Ab), examining each tumor nest in the tissue section for staining, and assigning to the tissue section one or both of a modified H score (MHS) and a modified proportion score (MPS). If both of the MHS and MPS are assigned, the assignments may be performed in either order or simultaneously.

To assign the MHS, four separate percentages are estimated across all of the viable tumor cells and stained mononuclear inflammatory cells in all of the examined tumor nests: (a) cells that have no staining (intensity=0), (b) weak staining (intensity=1+), (c) moderate staining (intensity=2+) and (d) strong staining (intensity=3+). A cell must have at least partial membrane staining to be included in the weak, moderate or strong staining percentages. The estimated percentages, the sum of which is 100%, are then input into the formula of 1×(percent of weak staining cells)+2× (percent of moderate staining cells)+3×(percent of strong staining cells), and the result is assigned to the tissue section as the MHS.

The MPS is assigned by estimating, across all of the viable tumor cells and stained mononuclear inflammatory cells in all of the examined tumor nests, the percentage of cells that have at least partial membrane staining of any intensity, and the resulting percentage is assigned to the tissue section as the MPS. In one embodiment, estimating the percentage comprises selecting the percentage from the group consisting of: 0, 1, 2, 5, 10, 15, 20, 30, 40, 50, 60, 70, 80, 85, 90, 95 and 100 that the observer determines best represents the proportion of the examined cells are positive for membrane staining.

In some embodiments, the scoring process of the invention further comprises examining the stroma surrounding each tumor nest for the presence or absence of a band of anti-membrane-stained cells within the stroma. If the band is detected in the stroma surrounding at least one tumor nest, then the tissue section is assigned a stroma score (SS) of positive. A stroma score (SS) of negative is assigned to the tissue section if the band is not detected.

In one preferred embodiment, the scoring process of the invention is used to score PD-L1 expression in a tissue section of a tumor sample obtained from a patient diagnosed with non-small cell lung carcinoma (NSCLC), head and neck squamous carcinoma, or transitional cell carcinoma of the bladder (TCC), and in this embodiment, the process further comprises designating the tumor sample as positive or negative for PD-L1 expression. The tumor sample is designated as positive if the tissue section has any one or more for the following score assignments: (i) the SS is positive; (ii) the MHS is greater than zero, and (iii) the MPS is greater than zero. The tumor sample is designated as negative if the tissue section has any one or more of the following score assignments: (iv) the SS is negative and the MHS is zero; (v) the SS is negative and the MPS is zero; and (vi) the SS is negative, the MHS is zero and the MPS is zero.

In another preferred embodiment, the scoring process of the invention is used to score PD-L1 expression in a tissue section of a tumor sample obtained from a patient diagnosed with melanoma or breast cancer, and the process further comprises examining each tumor nest for the presence or absence of a lattice pattern of membrane-stained dendriform cells within the tumor nest. If the lattice pattern is detected in at least one of the tumor nests, the tissue section is assigned a dendriform pattern score (DS) of positive. A DS of negative is assigned to the tissue section if the lattice pattern is not detected in any of the tumor nests.

In some preferred embodiments, the stroma, DS, and one or both of the MHS and MPS scores assigned to a tissue section from melanoma or breast cancer are used to designate the tumor sample as positive or negative for PD-L1 expression. The tumor sample is designated as positive if the tissue section has any one or more for the following score assignments: (i) the stroma score is positive; (ii) the DS is positive; (iii) the MHS is greater than zero, and (iv) the MPS is greater than zero. The tumor sample is designated as negative if the tissue section has any one or more of the following score assignments: (v) the stroma score is negative, the DS is negative and the MHS is zero; (vi) the stroma score is negative, the DS is negative and the MPS is zero; and (vii) the stroma score is negative, the DS is negative, the MHS is zero and the MPS is zero.

In another aspect, the invention provides a method of designating a tumor sample as PD-L1 positive or PD-L1 negative. The method comprises (a) obtaining a tissue section from the tumor sample that has been stained with an antibody that binds to the PD-L1 protein (anti-PD-L1 Ab), (b) examining each tumor nest in the tissue section for staining, (c) assigning to the tissue section a modified proportion score (MPS), (d) examining the stroma surrounding each tumor nest for the presence or absence of a band of anti-membrane-stained cells within the stroma, (e) assigning to the tissue section a stroma score (SS) of positive or negative, wherein a positive SS is assigned if the band is detected and a negative stroma score (SS) is assigned to the tissue section if the band is not detected, and designating the tumor sample as PD-L1 positive if the assigned MPS is greater than 0 or if the assigned SS is positive, and designating the tumor sample as PD-L1 negative if the assigned MPS is 0 and the assigned SS is negative. In an embodiment, the tumor sample is selected from the group consisting of gastric cancer, bladder cancer, melanoma, NSCLC, head and neck cancer, colon or rectal adenocarcinoma, Hodgkins lymphoma, non-Hodgkins lymphoma, multiple myeloma, Myelodysplastic syndrome (MDS), anal canal squamous cell carcinoma, pancreas adenocarcinoma, esophageal squamous cell carcinoma or adenocarcinoma, biliary tract adenocarcinoma (gallbladder and biliary tree but excluding ampulla of vater cancers), carcinoid tumors, neuroendocrine carcinomas, well or moderately differentiated pancreatic neuroendocrine tumor, estrogen receptor (ER) positive HER2 negative breast cancer, HER2 positive breast cancer, triple negative breast cancer, ovarian epithelial, fallopian tube or primary peritoneal carcinoma, endometrial carcinoma, cervical squamous cell cancer, vulvar squamous cell carcinoma, small cell lung cancer, mesothelioma (malignant pleural esothelioma), thyroid cancer, including of papillary or follicular subtype, salivary gland carcinoma, nasopharyngeal carcinoma, glioblastoma multiforme, leiomyosarcoma, prostate adenocarcinoma.

In another aspect, the present invention provides a method for predicting if a human patient diagnosed with non-small cell lung carcinoma (NSCLC) is likely to respond to treatment with a PD-1 antagonist. The process comprises obtaining one or both of an MHS and an MPS for a tumor sample removed from the patient, wherein the MHS and MPS are obtained by performing the scoring process described above, and predicting the patient as likely to respond to the treatment if the obtained MHS and/or MPS is at or above a specified threshold or predicting the patient as not likely to respond to the treatment if each of the obtained MHS and MPS is below the specified threshold. In one preferred embodiment, the specified thresholds are MHS=190 and MPS=90.

In a still further aspect, the MHS and/or the MPS determined in accordance with the scoring process described above are used in a method of treating a human patient diagnosed with NSCLC. The method comprises obtaining a diagnostic report that provides one or both of a modified H score (MHS) and a modified proportion score (MPS) for PD-L1 expression for a NSCLC tumor sample removed from the patient. The patient is treated with a chemotherapeutic regimen comprising a PD-1 antagonist if one or both of the MHS and the MPS is at or above a specified threshold. However, if each of the MHS and MPS are below the specified threshold, the patient is treated with a chemotherapeutic regimen that does not include a PD-1 antagonist. The specified threshold for MHS is greater than zero, and the specified threshold for MPS is greater than zero. In one preferred embodiment, specified thresholds are MHS=190 and MPS=90.

In any of the aspects and embodiments of the invention described above or elsewhere herein, the estimated percentages used in assigning one of both of the MHS and the MPS is preferably confined to a discrete estimate selected from the group consisting of 0, 1, 2, 5, 10, 15, 20, 30, 40, 50, 60, 70, 80, 85, 90, 95 and 100.

In any of the aspects and embodiments of the invention described above or elsewhere herein, the tissue section is preferably a formalin-fixed, paraffin-embedded tissue section.

In any of the aspects and embodiments of the invention described above or elsewhere herein, the anti-PD-L1 Ab used for staining the tissue section is preferably the monoclonal antibody 22C3.

In any of the response prediction and treatment methods described above or elsewhere herein, the PD-1 antagonist is preferably an anti-PD-1 antibody which comprises a heavy chain and a light chain, and wherein the heavy chain comprises the amino acid sequence shown in FIG. 9 (SEQ ID NO:32) and the light chain comprises the amino acid sequence shown in FIG. 10 (SEQ ID NO:33).

BRIEF DESCRIPTION OF THE DRAWINGS

(FIG. 4C); MHS=30, MPS=10, SS=positive and DS=negative; (FIG. 4D); MHS=50, MPS=20, SS=negative and DS=positive (FIG. 4E).

FIG. 5C showing PD-L1 staining in the tumor. The scoring process of the invention was used to assign the following scores to each displayed field: MHS=50, MPS=20, SS=negative, DS=positive (FIG. 5A); MHS=10, MPS=5, SS=positive and DS=negative (FIG. 5B); and MHS=260, MPS=100, SS=negative and DS=negative (FIG. 5C).

FIG. 7 shows the nucleotide sequences for antibody variable light and heavy chain cDNA (SEQ ID NO:7 and SEQ ID NO:15) prepared from total RNA isolated from hybridoma MEB037.20C3 and the predicted amino acid sequences encoded thereby (bold font) (SEQ ID NO:5 and SEQ ID NO:13), with brackets indicating nucleotide and amino acid sequences for the leader peptide and underlining indicating the CDR sequences.

FIG. 8 shows the nucleotide sequences for antibody variable light and heavy chain cDNA (SEQ ID NO:22 and SEQ ID NO:30) prepared from total RNA isolated from hybridoma MEB037.22C3 and the predicted amino acid sequences encoded thereby (bold font) (SEQ ID NO:20 and SEQ ID NO:28, with brackets indicating nucleotide and amino acid sequences for the leader peptide and underlining indicating the CDR sequences.

FIGS. 9A and 9B show the amino acid sequence (SEQ ID NO:32) for the heavy chain of a preferred anti-PD-1 antibody useful in the treatment methods of the present invention, which corresponds to amino acid residues 20 to 466 of SEQ ID NO:31 set forth in U.S. Pat. No. 8,354,509.

FIG. 10 shows the amino acid sequence (SEQ ID NO:33) for the light chain of a preferred anti-PD-1 antibody useful in the treatment methods of the present invention, which corresponds to amino acid residues 20 to 237 of SEQ ID NO:36 set forth in U.S. Pat. No. 8,354,509.

DETAILED DESCRIPTION

Abbreviations

Figure 1:
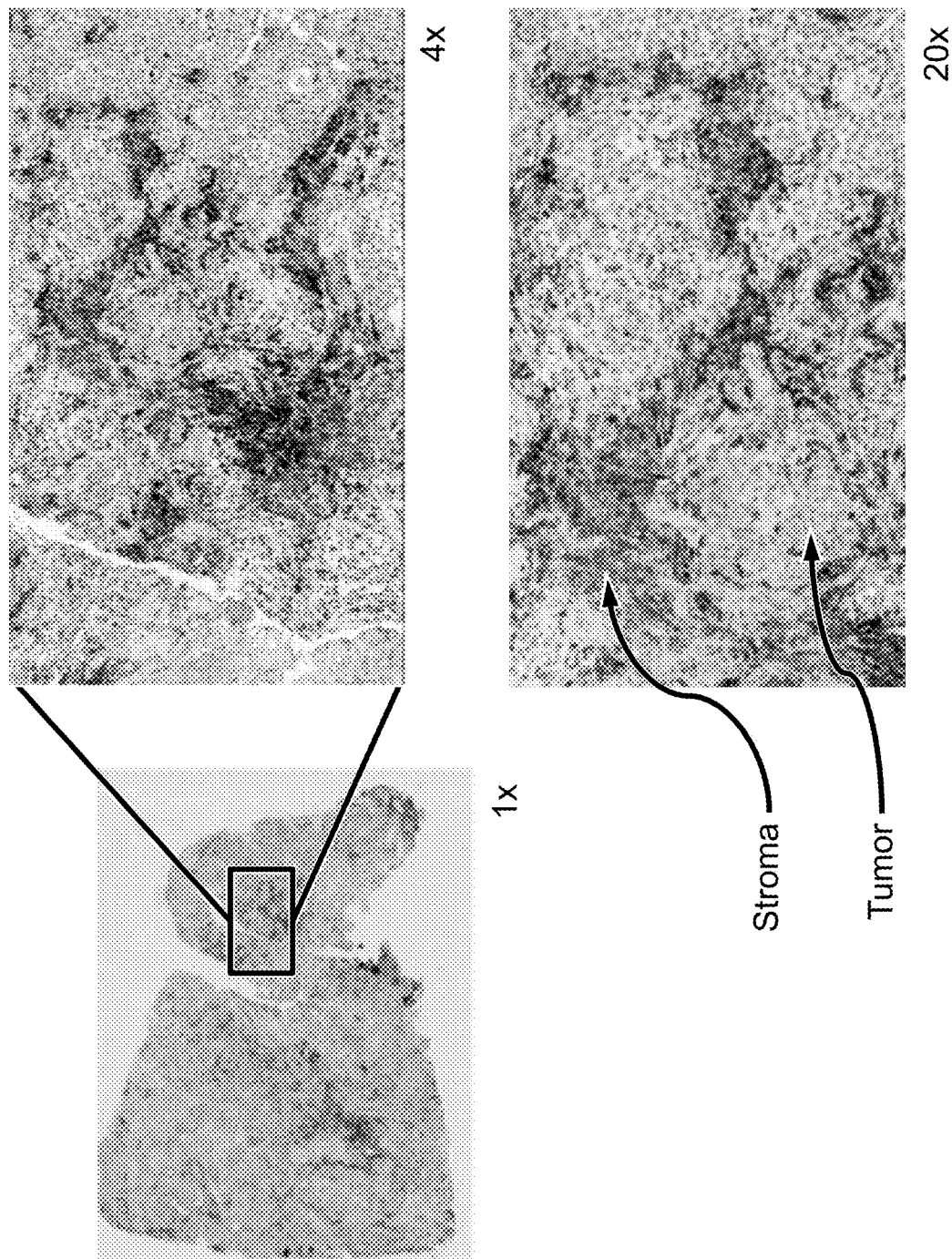
FIG. 1 shows images of an FFPE tissue section of NSCLC stained by IHC with the antibody 22C3, with the box indicating a particular field viewed at 1×, 4× and 20× magnification, and the arrows indicating PD-L1 expressing tumor cells and PD-L1 positive stroma in this field at 20× magnification. The scoring process of the invention was used to assign the following scores to the boxed field: MHS=10, MPS=5 and a SS=positive.

Throughout the detailed description and examples of the invention the following abbreviations will be used:
CDR Complementarity determining region in the immunoglobulin variable regions, defined using the Kabat numbering system, unless otherwise indicated
CHO Chinese hamster ovary
Clothia An antibody numbering system described in Al-Lazikani et al., *JMB* 273:927-948 (1997)
EC50 concentration resulting in 50% efficacy or binding
ELISA Enzyme-linked immunosorbant assay
FFPE formalin-fixed, paraffin-embedded
FR Antibody framework region: the immunoglobulin variable regions excluding the CDR regions.
HRP Horseradish peroxidase
IgG Immunoglobulin G
Kabat An immunoglobulin alignment and numbering system pioneered by Elvin A. Kabat ((1991) Sequences of Proteins of Immunological Interest, 5th Ed. Public Health Service, National Institutes of Health, Bethesda, Md.)
mAb or Mab or MAb Monoclonal antibody
MHS Modified H Score
MPS Modified Proportion Score
V region The segment of IgG chains which is variable in sequence between different antibodies. It extends to Kabat residue 109 in the light chain and 113 in the heavy chain.
VH Immunoglobulin heavy chain variable region
VK Immunoglobulin kappa light chain variable region Definitions So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

As used herein, including the appended claims, the singular forms of words such as "a," "an," and "the," include their corresponding plural references unless the context clearly dictates otherwise.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding compound, or by another cell. The term "subject" includes any organism, preferably an animal, more preferably a mammal (e.g., rat, mouse, dog, cat, rabbit) and most preferably a human.

As used herein, the term "antibody" refers to any form of antibody that exhibits the desired biological or binding activity. Thus, it is used in the broadest sense and specifically covers, but is not limited to, monoclonal antibodies (including full length monoclonal antibodies), polyclonal antibodies, multispecific antibodies (e.g., bispecific antibodies), humanized, fully human antibodies, chimeric antibodies and camelized single domain antibodies. "Parental antibodies" are antibodies obtained by exposure of an immune system to an antigen prior to modification of the antibodies for an intended use, such as humanization of an antibody for use as a human therapeutic antibody.

In general, the basic antibody structural unit comprises a tetramer. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of the heavy chain may define a constant region primarily responsible for effector function. Typically, human light chains are classified as kappa and lambda light chains. Furthermore, human heavy chains are typically classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989).

The variable regions of each light/heavy chain pair form the antibody binding site. Thus, in general, an intact antibody has two binding sites. Except in bifunctional or bispecific antibodies, the two binding sites are, in general, the same.

Typically, the variable domains of both the heavy and light chains comprise three hypervariable regions, also called complementarity determining regions (CDRs), located within relatively conserved framework regions (FR). The CDRs are usually aligned by the framework regions, enabling binding to a specific epitope. In general, from N-terminal to C-terminal, both light and heavy chains variable domains comprise FR1, CDR1, FR2, CDR2, FR3, CDR3 and FR4. The assignment of amino acids to each domain is, generally, in accordance with the definitions of *Sequences of Proteins of Immunological Interest*, Kabat, et al.; National Institutes of Health, Bethesda, Md.; 5th ed.; NIH Publ. No. 91-3242 (1991); Kabat (1978) Adv. Prot. Chem. 32:1-75; Kabat, et al., (1977) J. Biol. Chem. 252: 6609-6616; Chothia, et al., (1987) J Mol. Biol. 196:901-917 or Chothia, et al., (1989) Nature 342:878-883.

As used herein, the term "hypervariable region" refers to the amino acid residues of an antibody that are responsible for antigen-binding. The hypervariable region comprises amino acid residues from a "complementarity determining region" or "CDR" (i.e. CDRL1, CDRL2 and CDRL3 in the light chain variable domain and CDRH1, CDRH2 and CDRH3 in the heavy chain variable domain). See Kabat et al. (1991) Sequences of Proteins of Immunological Interest, 5th Ed. Public Health Service, National Institutes of Health, Bethesda, Md. (defining the CDR regions of an antibody by sequence); see also Chothia and Lesk (1987) *J. Mol. Biol.* 196: 901-917 (defining the CDR regions of an antibody by structure). As used herein, the term "framework" or "FR" residues refers to those variable domain residues other than the hypervariable region residues defined herein as CDR residues.

As used herein, unless otherwise indicated, "antibody fragment" or "antigen binding fragment" refers to antigen binding fragments of antibodies, i.e. antibody fragments that retain the ability to bind specifically to the antigen bound by the full-length antibody, e.g. fragments that retain one or more CDR regions. Examples of antibody binding fragments include, but are not limited to, Fab, Fab', F(ab')$_2$, and Fv fragments; diabodies; linear antibodies; single-chain antibody molecules, e.g., sc-Fv; nanobodies and multispecific antibodies formed from antibody fragments.

As used herein, antibody 20C3 is (i) the antibody produced by hybridoma subclone MEB037.20C3.116 or (ii) a monoclonal antibody comprising the light chain and heavy chain mature variable regions set forth in Table 1 below.

TABLE 1

Characteristics of Monoclonal Antibody MEB037.20C3

| Antibody Feature | Amino Acid Sequence | SEQ ID NO |
|---|---|---|
| Light Chain | | |
| CDRL1 | KSSQSLLNSRTRKNYLA | 1 |
| CDRL2 | WASTRES | 2 |
| CDRL3 | QQSYDVVT | 3 |
| Leader Sequence | MDSQAQVLILLLLWVSGTFG | 4 |
| Variable Region | MDSQAQVLILLLLWVSGTFGDIVMSQSPSSLAVSAGEKVTMSCK SSQSLLNSRTRKNYLAWYQQKPGQSPKLLIYWASTRESGVPDRF TGSGSGTDFTLTISSVQAEDLAVYYCQQSYDVVTFGAGTKLELK | 5 |
| Mature Variable Region | DIVMSQSPSSLAVSAGEKVTMSCKSSQSLLNSRTRKNYLAWYQQ KPGQSPKLLIYWASTRESGVPDRFTGSGSGTDFTLTISSVQAED LAVYYCQQSYDVVTFGAGTKLELK | 6 |
| DNA Sequence Encoding the Variable Region | ATGGATTCACAGGCCCAGGTTCTTATATTGCTGCTGCTATGGGT ATCTGGTACCTTTGGGGACATTGTGATGTCACAATCTCCATCCT CCCTGGCTGTGTCAGCAGGAGAGAAGGTCACTATGAGCTGCAAA TCCAGTCAGAGTCTGCTCAACAGTAGAACCCGAAAGAACTACTT GGCTTGGTACCAGCAGAAACCAGGGCAGTCTCCTAAACTGCTGA TCTACTGGGCATCCACTAGGGAATCTGGGGTCCCTGATCGCTTC ACAGGCAGTGGATCTGGGACAGATTTCACTCTCACCATCAGCAG TGTGCAGGCTGAAGACCTGGCAGTTTATTACTGCCAGCAATCTT ATGATGTGGTCACGTTCGGTGCTGGGACCAAGCTGGAGCTGAAA | 7 |
| Heavy Chain | | |
| CDRH1 Kabat Def'n | SYWMH | 8 |
| CDRH1 Chothia Def'n | GYIFTSYWMH | 9 |
| CDRH2 | YINPSSDYNEYSEKFMD | 10 |
| CDRH3 | SGWLVHGDYYFDY | 11 |
| Leader Sequence | MERHWIFLFLFSVTAGVHS | 12 |
| Variable Region | MERHWIFLFLFSVTAGVHSQVQVQQSGAELAEPGASVKMSCKAS GYIFTSYWMHWLKQRPGQGLEWIGYINPSSDYNEYSEKFMDKAT LTADKASTTAYMQLISLTSEDSAVYYCARSGWLVHGDYYFDYWG QGTTLTVSS | 13 |
| Mature Variable Region | QVQVQQSGAELAEPGASVKMSCKASGYIFTSYWMHWLKQRPGQG LEWIGYINPSSDYNEYSEKFMDKATLTADKASTTAYMQLISLTS EDSAVYYCARSGWLVHGDYYFDYWGQGTTLTVSS | 14 |
| DNA Sequence Encoding Variable Region | ATGGAAAGGCACTGGATCTTTCTCTTCCTGTTTTCAGTAACTGC AGGTGTCCACTCCCAGGTCCAGGTTCAGCAGTCTGGGGCTGAAC TGGCAGAACCTGGGGCCTCAGTGAAGATGTCCTGCAAGGCCTCT GGCTACATCTTTACTAGCTACTGGATGCACTGGCTAAAGCAGAG GCCTGGACAGGGTCTGGAATGGATTGGATACATTAATCCCAGCA GTGATTATAATGAATACAGTGAGAAATTCATGGACAAGGCCACA TTGACTGCAGACAAAGCCTCCACCACAGCCTACATGCAACTGAT CAGCCTGACATCTGAGGACTCTGCAGTCTATTACTGTGCAAGAT CGGGATGGTTAGTACATGGAGACTATTATTTTGACTACTGGGGC CAAGGCACCACTCTCACAGTCTCCTCA | 15 |

As used herein, antibody 22C3 is (i) the antibody produced by hybridoma subclone MEB037.22C3.138 or (ii) a monoclonal antibody comprising the light chain and heavy chain mature variable regions set forth in Table 2 below.

TABLE 2

Characteristics of Monoclonal Antibody MEB037.22C3

| Antibody Feature | Amino Acid Sequence | SEQ ID NO |
|---|---|---|
| *Light Chain* | | |
| CDRL1 | KSSQSLLHTSTRKNYLA | 16 |
| CDRL2 | WASTRES | 17 |
| CDRL3 | KQSYDVVT | 18 |
| Leader Sequence | MDSQAQVLILLLLWVSGTCG | 19 |
| Variable Region | MDSQAQVLILLLLWVSGTCGDIVMSQSPSSLAVSAGEKVTMTCKSSQSL LHTSTRKNYLAWYQQKPGQSPKLLIYWASTRESGVPDRFTGSGSGTDFT LTISSVQAEDLAVYYCKQSYDVVTFGAGTKLELK | 20 |
| Mature Variable Region | DIVMSQSPSSLAVSAGEKVTMTCKSSQSLLHTSTRKNYLAWYQQKPGQS PKLLIYWASTRESGVPDRFTGSGSGTDFTLTISSVQAEDLAVYYCKQSY DVVTFGAGTKLELK | 21 |
| DNA Sequence Encoding Variable Region | ATGGATTCACAGGCCCAGGTTCTTATATTGCTGCTGCTATGGGTATCTG GTACCTGTGGGGACATTGTGATGTCACAGTCTCCCTCCTCCCTGGCTGT GTCAGCAGGAGAGAAGGTCACTATGACCTGCAAATCCAGTCAGAGTCTG CTCCACACTAGCACCCGAAAGAACTACTTGGCTTGGTACCAGCAGAAAC CAGGGCAGTCTCCTAAACTGCTGATCTATTGGGCATCCACTAGGGAATC TGGGGTCCCTGATCGCTTCACAGGCAGTGGATCTGGGACAGATTTCACT CTCACCATCAGCAGTGTGCAGGCTGAAGACCTGGCAGTTTATTACTGCA AACAATCTTATGATGTGGTCACGTTCGGTGCTGGGACCAAGCTGGAGCT GAAA | 22 |
| *Heavy Chain* | | |
| CDRH1 Kabat Def'n | SYWIH | 23 |
| CDRH1 Chothia Def'n | GTTFTSYWIH | 24 |
| CDRH2 | YINPSSGYHEYNQKFID | 25 |
| CDRH3 | SGWLIHGDYYFDF | 26 |
| Leader Sequence | MERHWIFLFLFSVTAGVHS | 27 |
| Variable Region | MERHWIFLFLFSVTAGVHSQVHLQQSGAELAKPGASVKMSCKASGYTFT SYWIHWIKQRPGQGLEWIGYINPSSGYHEYNQKFIDKATLTADRSSSTA YMHLTSLTSEDSAVYYCARSGWLIHGDYYFDFWGQGTTLTVSS | 28 |
| Mature Variable Region | QVHLQQSGAELAKPGASVKMSCKASGYTFTSYWIHWIKQRPGQGLEWIG YINPSSGYHEYNQKFIDKATLTADRSSSTAYMHLTSLTSEDSAVYYCAR SGWLIHGDYYFDFWGQGTTLTVSS | 29 |
| DNA Sequence Encoding Variable Region | ATGGAAAGGCACTGGATCTTTCTCTTCCTGTTTTCAGTAACTGCAGGTG TCCACTCCCAGGTCCACCTTCAGCAGTCTGGGGCTGAACTGGCAAAACC TGGGGCCTCAGTGAAGATGTCCTGCAAGGCTTCTGGCTACACGTTTACT AGTTACTGGATACACTGGATAAAGCAGAGGCCTGGACAGGGTCTGGAAT GGATTGGATACATTAATCCTTCCTCTGGTTATCATGAATACAATCAGAA ATTCATTGACAAGGCCACATTGACTGCTGACAGATCCTCCAGCACAGCC TACATGCACCTGACCAGCCTGACGTCTGAAGACTCTGCAGTCTATTACT GTGCAAGATCGGGATGGTTAATACATGGAGACTACTACTTTGACTTCTG GGGCCAAGGCACCACTCTCACAGTCTCCTCA | 30 |

The terms "cancer", "cancerous", or "malignant" refer to or describe the physiological condition in mammals that is typically characterized by unregulated cell growth. Examples of cancer include but are not limited to, carcinoma, lymphoma, leukemia, blastoma, and sarcoma. More particular examples of such cancers include squamous cell carcinoma, myeloma, small-cell lung cancer, non-small cell lung cancer, glioma, hodgkin's lymphoma, non-hodgkin's lymphoma, acute myeloid leukemia (AML), multiple myeloma, gastrointestinal (tract) cancer, renal cancer, ovarian cancer, liver cancer, lymphoblastic leukemia, lymphocytic leukemia, colorectal cancer, endometrial cancer, kidney cancer, prostate cancer, thyroid cancer, melanoma, chondrosarcoma, neuroblastoma, pancreatic cancer, glioblastoma multiforme, cervical cancer, brain cancer, stomach cancer, bladder cancer, hepatoma, breast cancer, colon carcinoma, and head and neck cancer. Particularly preferred cancers that may be analyzed or treated in accordance with the present invention include those characterized by elevated expression of PD-1 and/or its ligands PD-L1 and/or PD-L2 in tested tissue samples, such as ovarian, renal, colorectal, pancreatic, breast, liver, glioblastoma, non-small cell lung cancer, gastric, esophageal cancers, melanoma, head and neck cancer, and transitional cell cancer of the bladder.

A "chemotherapeutic agent" is a chemical compound or biological molecule useful in the treatment of cancer. Classes of chemotherapeutic agents include, but are not limited to: alkylating agents, antimetabolites, kinase inhibitors, spindle poison plant alkaloids, cytoxic/antitumor antibiotics, topisomerase inhibitors, photosensitizers, and antibodies and fusion proteins that block ligand/receptor signaling in any biological pathway that supports tumor maintenance and/or growth. Chemotherapeutic agents useful in the treatment methods of the present invention include cytostatic agnets, cytotoxic agents and immunotherapeutic agents.

"Conservatively modified variants" or "conservative substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity of the protein. Those of skill in this art recognize that, in general, single amino acid substitutions in non-essential regions of a polypeptide do not substantially alter biological activity (see, e.g., Watson et al. (1987) *Molecular Biology of the Gene*, The Benjamin/Cummings Pub. Co., p. 224 (4th Ed.)). In addition, substitutions of structurally or functionally similar amino acids are less likely to disrupt biological activity. Exemplary conservative substitutions are set forth in Table 3.

TABLE 3

Exemplary Conservative Amino Acid Substitutions

| Original residue | Conservative substitution |
| --- | --- |
| Ala (A) | Gly; Ser |
| Arg (R) | Lys; His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

Function-conservative variants of the antibodies of the invention are also contemplated by the present invention. "Function-conservative variants," as used herein, refers to antibodies or fragments in which one or more amino acid residues have been changed without altering a desired property, such an antigen affinity and/or specificity. Such variants include, but are not limited to, replacement of an amino acid with one having similar properties, such as the conservative amino acid substitutions of Table 3.

"Dendriform cell" in the context of a tumor tissue section stained in an IHC assay with an anti-PD-L1 Ab means a cell having numerous, branched surface projections resembling a tree. A dendriform cell may include, but is not limited to, any type of dendritic cell that forms part of the mammalian immune system.

"Homology" refers to sequence similarity between two polypeptide sequences when they are optimally aligned. When a position in both of the two compared sequences is occupied by the same amino acid monomer subunit, e.g., if a position in a light chain CDR of two different Abs is occupied by alanine, then the two Abs are homologous at that position. The percent of homology is the number of homologous positions shared by the two sequences divided by the total number of positions compared×100. For example, if 8 of 10 of the positions in two sequences are matched or homologous when the sequences are optimally aligned then the two sequences are 80% homologous. Generally, the comparison is made when two sequences are aligned to give maximum percent homology. For example, the comparison can be performed by a BLAST algorithm wherein the parameters of the algorithm are selected to give the largest match between the respective sequences over the entire length of the respective reference sequences.

The following references relate to BLAST algorithms often used for sequence analysis: BLAST ALGORITHMS: Altschul, S. F., et al., (1990) J. Mol. Biol. 215:403-410; Gish, W., et al., (1993) Nature Genet. 3:266-272; Madden, T. L., et al., (1996) Meth. Enzymol. 266:131-141; Altschul, S. F., et al., (1997) Nucleic Acids Res. 25:3389-3402; Zhang, J., et al., (1997) Genome Res. 7:649-656; Wootton, J. C., et al., (1993) Comput. Chem. 17:149-163; Hancock, J. M. et al., (1994) Comput. Appl. Biosci. 10:67-70; ALIGNMENT SCORING SYSTEMS: Dayhoff, M. O., et al., "A model of evolutionary change in proteins." in Atlas of Protein Sequence and Structure, (1978) vol. 5, suppl. 3. M. O. Dayhoff (ed.), pp. 345-352, Natl. Biomed. Res. Found., Washington, D.C.; Schwartz, R. M., et al., "Matrices for detecting distant relationships." in Atlas of Protein Sequence and Structure, (1978) vol. 5, suppl. 3." M. O. Dayhoff (ed.), pp. 353-358, Natl. Biomed. Res. Found., Washington, D.C.; Altschul, S. F., (1991) J. Mol. Biol. 219:555-565; States, D. J., et al., (1991) Methods 3:66-70; Henikoff, S., et al., (1992) Proc. Natl. Acad. Sci. USA 89:10915-10919; Altschul, S. F., et al., (1993) J. Mol. Evol. 36:290-300; ALIGNMENT STATISTICS: Karlin, S., et al., (1990) Proc. Natl. Acad. Sci. USA 87:2264-2268; Karlin, S., et al., (1993) Proc. Natl. Acad. Sci. USA 90:5873-5877; Dembo, A., et al., (1994) Ann. Prob. 22:2022-2039; and Altschul, S. F. "Evaluating the statistical significance of multiple distinct local alignments." in Theoretical and Computational Methods in Genome Research (S. Suhai, ed.), (1997) pp. 1-14, Plenum, N.Y.

"Isolated antibody" refers to the purification status and in such context means the molecule is substantially free of other biological molecules such as nucleic acids, proteins, lipids, carbohydrates, or other material such as cellular debris and growth media. Generally, the term "isolated" is not intended to refer to a complete absence of such material or to an absence of water, buffers, or salts, unless they are present in amounts that substantially interfere with experimental or therapeutic use of the binding compound as described herein.

The term "monoclonal antibody", as used herein, refers to a population of substantially homogeneous antibodies, i.e., the antibody molecules comprising the population are identical in amino acid sequence except for possible naturally occurring mutations that may be present in minor amounts. In contrast, conventional (polyclonal) antibody preparations typically include a multitude of different antibodies having different amino acid sequences in their variable domains, particularly their CDRs, which are often specific for different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) Nature 256: 495, or may be made by recombinant DNA methods (see, e.g., U.S. Pat. No. 4,816,567). The "monoclonal antibodies" may also be isolated from phage antibody libraries using the techniques described in Clackson et al. (1991) Nature 352: 624-628 and Marks et al. (1991) J. Mol. Biol. 222: 581-597, for example. See also Presta (2005) J. Allergy Clin. Immunol. 116:731.

"Patient" or "subject" refers to any single subject for which therapy is desired or that is participating in a clinical trial, epidemiological study or used as a control, including humans and mammalian veterinary patients such as cattle, horses, dogs, and cats.

"PD-1 antagonist" means any chemical compound or biological molecule that blocks binding of PD-L1 to PD-1, and includes antibodies and fusion proteins that bind to PD-1 or PD-L1. Examples of PD-1 antagonists include any anti-PD-1 antibody described in U.S. Pat. Nos. 8,008,449, 7,521,051 and 8,354,509, any anti-PD-L1 antibody described in U.S. Pat. No. 8,383,796, BMS-936558 (nivolumab), MPDL3280A, CT-011, ONO-4538, BMS-936559, MEDI4736, AMP-224, and an anti-PD-1 antibody comprising the heavy and light chain amino acid sequences shown in FIGS. 9 and 10 herein.

"Primary anti-PD-L1 antibody" refers to an antibody that binds specifically to PD-L1 in a tissue section, and is generally the first antibody used in an IHC assay of PD-L1 expression in a tumor sample. In one embodiment, the primary antibody is the only antibody used in the IHC assay.

"Secondary antibody" refers to an antibody that binds specifically to a primary anti-PD-L1 antibody, thereby forming a bridge between the primary antibody and a subsequent detection reagent, if any. The secondary antibody is generally the second antibody used in an IHC assay of PD-L1 expression in a tumor sample.

The term "therapeutically effective amount" refers to an amount of a chemotherapeutic effective to "treat" a cancer in a subject or mammal by achieving at least one positive therapeutic effect, such as for example, reduced number of cancer cells, reduced tumor size, reduced rate of cancer cell infiltration into peripheral organs, and reduced rate of tumor metastasis or tumor growth. Positive therapeutic effects in cancer can be measured in a number of ways (See, W. A. Weber, J. Nucl. Med. 50:1S-10S (2009)). For example, with respect to tumor growth inhibition, according to NCI standards, a T/C≤42% is the minimum level of anti-tumor activity. A T/C<10% is considered a high anti-tumor activity level, with T/C (%)=Median tumor volume of the treated/Median tumor volume of the control×100. In some embodiments, the treatment achieved by a therapeutically effective amount is progression free survival (PFS), disease free survival (DFS) or overall survival (OS). PFS, also referred to as "Time to Tumor Progression" indicates the length of time during and after treatment that the cancer does not grow, and includes the amount of time patients have experienced a complete response or a partial response, as well as the amount of time patients have experienced stable disease. DFS refers to the length of time during and after treatment that the patient remains free of disease. OS refers to a prolongation in life expectancy as compared to naive or untreated individuals or patients.

"Tissue Section" refers to a single part or piece of a tissue sample, e.g., a thin slice of tissue cut from a sample of a normal tissue or of a tumor. It is understood that multiple sections of a single tissue sample may be prepared and analyzed in accordance with the present invention.

"Treat" or "treating" means to administer a therapeutic agent, such as a composition containing any of the antibodies or antigen binding fragments of the present invention, internally or externally to a subject or patient having one or more disease symptoms, or being suspected of having a disease, for which the agent has therapeutic activity. Typically, the agent is administered in an amount effective to alleviate one or more disease symptoms in the treated subject or population, whether by inducing the regression of or inhibiting the progression of such symptom(s) by any clinically measurable degree. The amount of a therapeutic agent that is effective to alleviate any particular disease symptom (also referred to as the "therapeutically effective amount") may vary according to factors such as the disease state, age, and weight of the patient, and the ability of the drug to elicit a desired response in the subject. Whether a disease symptom has been alleviated can be assessed by any clinical measurement typically used by physicians or other skilled healthcare providers to assess the severity or progression status of that symptom. While an embodiment of the present invention (e.g., a treatment method or article of manufacture) may not be effective in alleviating the target disease symptom(s) in every subject, it should alleviate the target disease symptom(s) in a statistically significant number of subjects as determined by any statistical test known in the art such as the Student's t-test, the chi$^2$-test, the U-test according to Mann and Whitney, the Kruskal-Wallis test (H-test), Jonckheere-Terpstra-test and the Wilcoxon-test.

"Treatment," as it applies to a human, veterinary, or research subject, refers to therapeutic treatment, as well as research and diagnostic applications. "Treatment" as it applies to a human, veterinary, or research subject, or cell, tissue, or organ, encompasses contact of the antibodies or antigen binding fragments of the present invention to a human or animal subject, a cell, tissue, physiological compartment, or physiological fluid.

"Tumor", as it applies to a subject diagnosed with, or suspected of having, a cancer, means a malignant or potentially malignant neoplasm or tissue mass of any size, and includes primary tumors and secondary neoplasms.

General

The present invention provides processes for scoring PD-L1 expression in tumor tissue sections that have been stained with an anti-PD-L1 antibody in an IHC assay. The results of these scoring processes may be used to select patients for treatment with a PD-1 antagonist, e.g., as enrollment criteria in a clinical trial, to predict response of a subject to a PD-1 antagonist, and in methods of treating a patient for cancer.

Sample Collection and Preparation of Tissue Sections

A tumor tissue sample used to prepare stained tissue sections for scoring PD-L1 expression can be collected from a subject before and/or after exposure of the subject to one or more therapeutic agents, e.g. a PD-1 antagonist or other chemotherapeutic agent. Accordingly, tumor samples may be collected from a subject over a period of time. The tumor sample can be obtained by a variety of procedures including, but not limited to, surgical excision, aspiration or biopsy. The tissue sample may be sectioned and examined for PD-L1 as a fresh specimen. In other embodiments, the tissue sample is frozen for further sectioning. In other embodiments, the tissue sample is preserved by fixing and embedding in paraffin or the like.

The tissue sample may be fixed by conventional methodology, with the length of fixation depending on the size of the tissue sample and the fixative used. Neutral buffered formalin, glutaraldehyde, Bouin's or paraformaldehyde are nonlimiting examples of fixatives. In preferred embodiments, the tissue sample is fixed with formalin. In some embodiments, the fixed tissue sample is also embedded in paraffin to prepare a formalin-fixed and paraffin-embedded (FFPE) tissue sample. Examples of paraffin include, but are not limited to, Paraplast, Broloid and Tissuemay.

Typically, the tissue sample is fixed and dehydrated through an ascending series of alcohols, infiltrated and embedded with paraffin or other sectioning media so that the tissue sample may be sectioned. Alternatively, the tumor tissue sample is first sectioned and then the individual sections are fixed.

In some embodiments, the scoring process of the invention is performed on FFPE tissue sections of about 3-4 millimeters, and preferably 4 micrometers, which are mounted and dried on a microscope slide.

Immunohistochemistry

An IHC assay typically begins with antigen retrieval, which may vary in terms of reagents and methods. The antigen retrieval process may involve pressure cooking, protease treatment, microwaving, or heating histologic sections in baths of appropriate buffers, with the standard goal of unmasking antigens hidden by formalin crosslinks or other fixation. See, e.g., Leong et al. *Appl. Immnunohistochem.* 4(3):201 (1996).

Two general methods of IHC may be used; direct and indirect assays. In a direct IHC assay, binding of antibody to the target antigen is determined directly. This direct assay uses a labeled reagent, such as a fluorescent tag or an enzyme-labeled primary antibody, which can be visualized without further antibody interaction. In a typical indirect assay, unconjugated primary antibody binds to the antigen and then a labeled secondary antibody binds to the primary antibody. Where the secondary antibody is conjugated to an enzymatic label, a chromagenic or fluorogenic substrate is added to provide visualization of the antigen. Signal amplification occurs because several secondary antibodies may react with different epitopes on the primary antibody.

The primary and/or secondary antibody used for immunohistochemistry typically will be labeled with a detectable moiety. Numerous labels are available which can be generally grouped into the following categories:
(a) Radioisotopes, such as $^{35}S$, $^{14}C$, $^{125}I$, $^{3}H$, and $^{131}I$. The antibody can be labeled with the radioisotope using the techniques described in *Current Protocols in Immunology*, Volumes 1 and 2, Coligen et al., Ed. Wiley-Interscience, New York, N.Y., Pubs. (1991) for example and radioactivity can be measured using scintillation counting. Other radionuclides include $^{99}Tc$, $^{90}Y$, $^{111}In$, $^{32}P$, $^{11}C$, $^{15}O$, $^{13}N$, $^{18}F$, $^{51}Cr$, $^{57}To$, $^{226}Ra$, $^{60}Co$, $^{59}Fe$, $^{57}Se$, $^{152}Eu$, $^{67}CU$, $^{217}Ci$, $^{211}At$, $^{212}Pb$, $^{47}Sc$, $^{109}Pd$, $^{234}Th$, and $^{40}K$, $^{157}Gd$, $^{55}Mn$, $^{52}Tr$, and $^{56}Fe$.
(b) Colloidal gold particles.
(c) Fluorescent or chemilluminescent labels including, but not limited to, rare earth chelates (europium chelates), fluorescein and its derivatives, rhodamine and its derivatives, isothiocyanate, phycoerythrin, phycocyanin, allophycocyanin, o-phthaladehyde, fluorescamine, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, Texas Red, dansyl, Lissamine, umbelliferone, phycocrytherin, phycocyanin, or commercially available fluorophores such SPECTRUM ORANGE® and SPECTRUM GREEN® and/or derivatives of any one or more of the above. The fluorescent labels can be conjugated to the antibody using the techniques disclosed in *Current Protocols in Immunology*, supra, for example. Fluorescence can be quantified using a fluorimeter.

Various enzyme-substrate labels are available and U.S. Pat. No. 4,275,149 provides a review of some of these. The enzyme generally catalyzes a chemical alteration of the chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor.

Examples of enzymatic labels include luciferases (e.g. firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al., Methods for the Preparation of Enzyme-Antibody Conjugates for use in Enzyme Immunoassay, in *Methods in Enzym.* (ed J. Langbne & H. Van Vunakis), Academic press, New York, 73:147-166 (1981).

Numerous enzyme-substrate combinations are available to those skilled in the art. For a general review of these, see U.S. Pat. Nos. 4,275,149 and 4,318,980. Examples of enzyme-substrate combinations are:
(i) Horseradish peroxidase (HRP) with hydrogen peroxidase as a substrate, wherein the hydrogen peroxidase oxidizes a dye precursor, such as, e.g., 3,3' diamino benzidine (DAB), which produces a brown end product; 3-amino-9-ethylcarbazole (AEC), which upon oxidation forms a rose-red end product; 4-chloro-1-napthol (CN), which precipitates as a blue end product; and p-Phenylenediamine dihydrochloride/pyrocatecol, which generates a blue-black product; orthophenylene diamine (OPD) and 3,3',5,5'-tetramethyl benzidine hydrochloride (TMB);
(ii) alkaline phosphatase (AP) and para-Nitrophenyl phosphate, naphthol AS-MX phosphate, Fast Red TR and Fast Blue BB, napthol AS-BI phosphate, napthol AS-TR phosphate, 5-bromo-4-chloro-3-indoxyl phosphate (BCIP), Fast Red LB, Fast Garnet GBC, Nitro Blue Tetrazolium (NBT), and iodonitrotetrazolium violet (INT); and
(iii) β-D-galactosidase (β-D-Gal) with a chromogenic substrate (e.g., p-nitrophenyl-β-D-galactosidase) or fluorogenic substrate (e.g., 4-methylumbelliferyl-β-D-galactosidase).

Any method known in the art for conjugating the antibody molecules to the various moieties may be employed, including those methods described by Hunter, et al., (1962) *Nature* 144:945; David, et al., (1974) *Biochemistry* 13:1014; Pain, et al., (1981) J. Immunol. Meth. 40:219; and Nygren, J., (1982) *Histochem. and Cytochem.* 30:407.

In some embodiments, the label is indirectly conjugated with the antibody. The skilled artisan will be aware of various techniques for achieving this. For example, the antibody can be conjugated with biotin and any of the four broad categories of labels mentioned above can be conjugated with avidin, or vice versa. Biotin binds selectively to avidin and thus, the label can be conjugated with the antibody in this indirect manner. Alternatively, to achieve indirect conjugation of the label with the antibody, the antibody is conjugated with a small hapten and one of the different types of labels mentioned above is conjugated with an anti-hapten antibody. Thus, indirect conjugation of the label with the antibody can be achieved.

After antigen retrieval and an optional blocking step, the tissue section is exposed to an anti-PD-L1 antibody as the primary antibody for a sufficient period of time and under suitable conditions to allow the primary antibody to bind to the PD-L1 protein in the tissue section. Appropriate conditions for achieving this can be determined by routine experimentation, with one example of suitable conditions described in Example 1 below. The slide is then washed to remove unbound and excess amounts of the primary antibody.

In some embodiments, the primary antibody is linked to a detectable label, such as paramagnetic ions, radioactive isotopes, fluorochromes, and NMR-detectable substances, and the slide is evaluated for PD-L1 staining using the appropriate imaging apparatus.

In other embodiments, immune complexes between PD-L1 and the primary antibody may be detected using a second binding agent that is linked to a detectable label. The second binding agent is preferably a secondary antibody, which is applied to the slide at a concentration and for a period of time sufficient to allow the formation of secondary immune complexes. The slide is then typically washed to remove any non-specifically bound secondary antibody, and the label in the secondary immune complexes is detected.

The secondary antibody may be labeled using avidin, strepavidin or biotin, which is independently labeled with a detectable moiety, such as a fluorescent dye (stain), a luminescent dye or a non-fluorescent dye. In principle, any enzyme that can be conjugated to or can bind indirectly to the secondary antibody (e.g., via conjugated avidin, strepavidin, biotin) could be used. The enzyme employed can be, for example, alkaline phosphatase (AP), horseradish peroxidase (HRP), beta-gal actosidase and/or glucose oxidase. The enzyme can also be directed at catalyzing a luminescence reaction of a substrate, such as, but not limited to, luciferase and aequorin, having a substantially non-soluble reaction product capable of luminescencing or of directing a second reaction of a second substrate, such as but not limited to, luciferine and ATP or coelenterazine and Ca. sup.++, having a luminescencing product. Finally, a detection reagent is applied that includes a chromagen or a fluorescently tagged molecule to visualize the localization of the immune complexes.

The IHC assay may be performed using an automated pathology system, which may include automated staining (conventional stains, histochemical techniques, immunostainers); automated in situ hybridization systems; automatic slide preparation (coverslip, slide drying) and integrated slide and cassette labeling, as described in Roja et al., Review of imaging solutions for integrated, quantitative immunohistochemistry in the Pathology daily practice, Folia Histochemica et Cytobiologica, Vol. 47, No. 3, 349-354, 2009.

A preferred IHC assay employs the commercially available Dako EnVision™ FLEX detection system, which is intended for use together with a Dako Autostainer instrument (Dako, an Agilent Technologies Company, Glostrup, Denmark). These reagents can be used off the shelf for other autostainers or for manually-performed staining (not performed with an autostainer)

Anti-PD-L1 Antibodies Used in Immunohistochemistry

The primary antibody is an anti-PD-L1 antibody, or antigen binding fragment thereof, which binds to the mature form of PD-L1 (lacking the presecretory leader sequence, also referred to as leader peptide) that is expressed on the surface of certain mammalian cells. The terms "PD-L1" and "mature PD-L1" are used interchangeably herein, and shall be understood to mean the same molecule unless otherwise indicated or readily apparent from the context. As used herein, an anti-human PD-L1 antibody or an anti-hPD-L1 antibody refers to an antibody that specifically binds to mature human PD-L1. A mature human PD-L1 molecule consists of amino acids 19-290 of the following sequence:

(SEQ ID NO: 31)
MRIFAVFIFMTYWHLLNAFTVTVPKDLYVVEYGSNMTIECKFPVEKQLDL

AALIVYWEMEDKNIIQFVHGEEDLKVQHSSYRQRARLLKDQLSLGNAALQ

ITDVKLQDAGVYRCMISYGGADYKRITVKVNAPYNKINQRILVVDPVTSE

HELTCQAEGYPKAEVIWTSSDHQVLSGKTTTTNSKREEKLFNVTSTLRIN

TTTNEIFYCTFRRLDPEENHTAELVIPELPLAHPPNERTHLVILGAILLC

LGVALTFIFRLRKGRMMDVKKCGIQDTNSKKQSDTHLEET.

An antibody that "specifically binds to human PD-L1," or an antibody that "specifically binds to a polypeptide comprising the amino acid sequence of human PD-L1," is an antibody that exhibits preferential binding to human PD-L1 as compared to other antigens, but this specificity does not require absolute binding specificity. An anti-hPD-L1 antibody is considered "specific" for human PD-L1 if its binding is determinative of the presence of human PD-L1 in a sample, e.g. without producing undesired results such as false positives in an IHC diagnostic assay. Antibodies, or binding fragments thereof, useful as a primary antibody in the processes and methods of the present invention will bind to human PD-L1 with an affinity that is at least two fold greater, preferably at least ten times greater, more preferably at least 20-times greater, and most preferably at least 100-times greater than the affinity with any non-PD-L1 protein. As used herein, an antibody is said to bind specifically to a polypeptide comprising a given sequence, e.g. mature human PD-L1, if it binds to polypeptides comprising that sequence but does not bind to proteins lacking that sequence.

Tissue sections of tumor samples from human subjects may be scored for PD-L1 expression using any anti-hPD-L1 Ab that produces essentially the same staining results on an FFPE or frozen tissue section of a tumor sample from a human as produced by the 22C3 Ab. For example, it is contemplated that the scoring process of the present invention may be used to quantify PD-L1 expression detected by the 5H-1 antibody developed at Mayo Foundation for Medical Education and Research (Toplian et al., supra).

Typically, an anti-PD-L1 Ab or antigen binding fragment useful in scoring expression of human PD-L1 by IHC assay, will exhibit the same degree of specificity for human PD-L1 as the 22C3 antibody and retain at least 80%, 85%, 90%, 95% or 100% of its human PD-L1 binding affinity when that affinity is expressed on a molar basis. It is also intended that an anti-PD-L1 antibody or antigen binding fragment useful in the invention can include conservative or non conservative amino acid substitutions from the 22C3 Ab or 20C3 Ab (referred to as "conservative variants" or "function conserved variants" of the antibody) that do not substantially alter its binding specificity or affinity.

Methods of Making Antibodies and Antigen Binding Fragments Thereof

Anti-PD-L1 antibodies may be purified from a hybridoma culture by the following process. The hybridoma culture is clarified by depth filtration using 1.2 micrometer glass fiber and 0.2 micrometer cellulose acetate filter. An equal volume of 2× ProSepA Buffer (100 mM Boric Acid, 5M NaCl, pH 8.5) is added to the clarified harvest and the diluted harvest is loaded onto a 170 mL bed volume Protein-A column. The column is washed with 5 column volumes (CV) of 1×ProSepA Buffer (50 mM Boric Acid, 2.5M NaCl, pH 8.5), then washed with 2 CV of 1×PBS, and the anti-hPD-L1 antibody eluted with 5 CV of Elution Buffer (0.1M Glycine, pH 3.0). The elution fractions containing IgG are combined and the pH neutralized by adding 1/10th volume of 1.0M Tris, pH buffer. The neutralized antibody composition is then sterile filtered using a 10 kDa disposable TFF cassette. The antibody may be formulated for storage by diafiltration against 10 liter of formulation buffer (20 mM sodium acetate, 9% sucrose, pH 5.0) and using 20 volume changes. Using this protocol, antibody 22C3 at a concentration of about 5.0 mg/ml can be prepared with a purity of at least 98% by SDS-PAGE, SEC HPLC and C8 RP-HPLC measurements, and with endotoxin levels of less than 0.1 EU/ml and less than 0.02 EU/mg.

The anti-PD-L1 antibodies described herein may also be produced recombinantly (e.g., in an *E. coli*/T7 expression system as discussed above). In this embodiment, nucleic acids encoding the antibody molecules (e.g., $V_H$ or $V_L$) may be inserted into a pET-based plasmid and expressed in the *E. coli*/T7 system. There are several methods by which to produce recombinant antibodies which are known in the art. One example of a method for recombinant production of antibodies is disclosed in U.S. Pat. No. 4,816,567. Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, biolistic injection and direct microinjection of the DNA into nuclei. In addition, nucleic acid molecules may be introduced into mammalian cells by viral vectors. Methods of transforming cells are well known in the art. See, for example, U.S. Pat. Nos. 4,399,216; 4,912,040; 4,740,461 and 4,959,455.

Anti-PD-L1 antibodies can also be synthesized by any of the methods set forth in U.S. Pat. No. 6,331,415.

Mammalian cell lines available as hosts for expression of the antibodies or fragments described herein are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells, HEK-293 cells and a number of other cell lines. Mammalian host cells include human, mouse, rat, dog, monkey, pig, goat, bovine, horse and hamster cells. Cell lines of particular preference are selected through determining which cell lines have high expression levels. Other cell lines that may be used are insect cell lines, such as Sf9 cells, amphibian cells, bacterial cells, plant cells and fungal cells. When recombinant expression vectors encoding the heavy chain or antigen-binding portion or fragment thereof, the light chain and/or antigen-binding fragment thereof are introduced into mammalian host cells, the antibodies are produced by culturing the host cells for a period of time sufficient to allow for expression of the antibody in the host cells or, more preferably, secretion of the antibody into the culture medium in which the host cells are grown.

Antibodies can be recovered from the culture medium using standard protein purification methods. Further, expression of antibodies of the invention (or other moieties therefrom) from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, and 0 323 997 and European Patent Application No. 89303964.4.

A polyclonal antibody is an antibody which was produced among or in the presence of one or more other, non-identical antibodies. In general, polyclonal antibodies are produced from collections of different B-lymphocytes, e.g. the B-lymphocyte of an animal treated with an immunogen of interest, which produces a population of different antibodies that are all directed to the immunogen. Usually, polyclonal antibodies are obtained directly from an immunized animal, e.g. spleen, serum or ascites fluid.

The processes of the present invention further may use as the primary antibody an antigen-binding fragment of an anti-PD-L1 antibody. The antibody fragments include $F(ab)_2$ fragments, which may be produced by enzymatic cleavage of an IgG by, for example, pepsin. Fab fragments may be produced by, for example, reduction of $F(ab)_2$ with dithiothreitol or mercaptoethylamine. A Fab fragment is a $V_L$—$C_L$ chain appended to a $V_H$—$C_{H1}$ chain by a disulfide bridge. A $F(ab)_2$ fragment is two Fab fragments which, in turn, are appended by two disulfide bridges. The Fab portion of an $F(ab)_2$ molecule includes a portion of the $F_c$ region between which disulfide bridges are located. An $F_v$ fragment is a $V_L$ or $V_H$ region.

Immunoglobulins may be assigned to different classes depending on the amino acid sequences of the constant domain of their heavy chains. There are at least five major classes of immunoglobulins: IgA, IgD, IgE, IgG and IgM, and several of these may be further divided into subclasses (isotypes), e.g. IgG-1, IgG-2, IgG-3 and IgG-4; IgA-1 and IgA-2. The invention may employ antibodies and antigen binding fragments of any of these classes or subclasses of antibodies.

In one embodiment, the primary antibody comprises a heavy chain constant region, e.g. a human constant region, such as γ1, γ2, γ3, or γ4 human heavy chain constant region or a variant thereof. In another embodiment, the primary antibody comprises a light chain constant region, e.g. a human light chain constant region, such as lambda or kappa human light chain region or variant thereof. By way of example, and not limitation the human heavy chain constant region can be γ1 and the human light chain constant region can be kappa. In an alternative embodiment, the Fc region of the antibody is γ4 with a Ser228Pro mutation (Schuurman, J et. al., *Mol. Immunol.* 38: 1-8, 2001).

Scoring Process

After completing the staining process, the slide is analyzed for PD-L1 staining, either by a human, e.g., a pathologist, or a computer programmed to distinguish between specific and non-specific staining results. The analysis may be performed directly by viewing the slide through a microscope at low, medium (10-20×) and high power (40-60×), or by viewing high resolution images of the slide taken at low, medium and high power. Low and medium power is typically used to detect stained tumor nests, as well as stroma staining and dendriform pattern staining. Medium and high power is typically used to examine individual tumor nests to estimate the number and intensity of viable tumor and mononuclear inflammatory cells that exhibit at least partial membrane staining. In one embodiment, stained tumor cells that are outside of tumor nests are included in the percentages used for calculating the MHS and/or the MPS.

Diagnostic Testing for PD-L1 Expression

Each of the steps of obtaining a tissue sample, preparing one or more tissue sections therefrom for IHC assay, performing the IHC staining, and scoring the results may be performed by separate individuals/entities at the same or separate locations. For example, a surgeon may obtain by biopsy a tissue sample from a cancer patient's tumor and then send the tissue sample to a pathology lab, which may fix the tissue sample and then prepare one or more slides, each with a single tissue section, for IHC assay. The slide(s) may be analyzed by IHC soon after preparation, or stored for future assay. The lab that prepared a tissue section for IHC assay may conduct the assay or send the slide(s) to a different lab to conduct the assay. A pathologist or trained professional who scores the stained slide(s) for PD-L1 staining may work for the diagnostic lab, or may be an independent contractor. Alternatively, a single diagnostic lab obtains the tissue sample from the subject's physician or surgeon and then performs all of the steps involved in preparing tissue sections, staining the slide(s) and scoring PD-L1 expression in the stained tissue section(s) or sending the stained slide(s) to a trained professional for PD-L1 scoring.

In some embodiments, the individuals involved with preparing and analyzing the tissue section by IHC assay do not know the identity of the subject whose sample is being tested; i.e., the sample received by the laboratory is made anonymous in some manner before being sent to the laboratory. For example, the sample may be merely identified by a number or some other code (a "sample ID") and the results of the IHC assay is reported to the party ordering the test using the sample ID. In preferred embodiments, the link between the identity of a subject and the subject's tissue sample is known only to the individual or to the individual's physician.

In some embodiments, after the test results have been obtained, the diagnostic laboratory generates a test report, which may include any one or more of the following results: the tissue sample was positive or negative for PD-L1 expression, the MPS, the MHS, the tissue sample was positive or negative for stromal staining, and the tissue sample was positive or negative for dendriform pattern.

The test report may also include guidance on how to interpret the results for predicting if a subject is likely to respond to a PD-1 antagonist. For example, in one embodiment, the patient's tumor is from a NSLC and if the MPS or MHS is at or above a prespecified threshold, the test report may indicate that the patient has a PD-L1 expression score that is correlated with response or better response to treatment with a PD-1 antagonist, while if the MPS or MHS is below the threshold, then the test report indicates that the patient has a PD-L1 expression score that is correlated with no response or poor response to treatment with a PD-1 antagonist. In some embodiments, the prespecified threshold for PD-L1 expression in NSLC tissue samples is an MHS of 170, 175, 180, 185, 190, 195, 200, 205, 210, or any number between 170 and 210, and is preferably between 185 and 195. In other embodiments, the prespecified threshold for PD-L1 expression in NSLC tissue samples is an MPS of 80, 85, 90, 95, 100 or any number between 80 and 100, and is preferably between 85 and 95.

In some embodiments, the test report is a written document prepared by the diagnostic laboratory and sent to the patient or the patient's physician as a hard copy or via electronic mail. In other embodiments, the test report is generated by a computer program and displayed on a video monitor in the physician's office. The test report may also comprise an oral transmission of the test results directly to the patient or the patient's physician or an authorized employee in the physician's office. Similarly, the test report may comprise a record of the test results that the physician makes in the patient's file.

Treatment Methods

A physician may use PD-L1 expression score(s) as a guide in deciding how to treat a patient who has been diagnosed with a type of cancer that is susceptible to treatment with a PD-1 antagonist or other chemotherapeutic agent(s). Typically, the physician would order a diagnostic test to determine PD-L1 expression in a tumor tissue sample removed from the patient prior to initiation of treatment with the PD-1 antagonist or the other chemotherapeutic agent(s), but it is envisioned that the physician could order the first or subsequent tests at any time after the individual is administered the first dose of the PD-1 antagonist or other chemotherapeutic agent(s). In some embodiments, a physician may be considering whether to treat the patient with a pharmaceutical product that is indicated for patients whose tumor tests positive for PD-L1 expression. In some embodiments, if the patient is diagnosed with a type of cancer that is susceptible to treatment with a PD-1 antagonist and at least one chemotherapeutic agent that is not a PD-1 antagonist, the physician may select which chemotherapeutic agent to use based on the PD-L1 expression score for the patient's tumor obtained from the diagnostic laboratory. For example, if the reported PD-L1 expression score is at or above a threshold score that is correlated with response or better response to treatment with a PD-1 antagonist, the physician selects a chemotherapeutic regimen that includes at least the PD-1 antagonist (optionally in combination with one or more additional chemotherapeutic agents), and if the reported PD-L1 expression score is below a threshold score that is correlated with no response or poor response to treatment with a PD-1 antagonist, the physician selects a regimen that does not include any PD-1 antagonist.

In deciding how to use the PD-L1 test results in treating any individual patient, the physician may also take into account other relevant circumstances, such as the type of cancer to be treated, the age, weight, gender, genetic background and race of the patient, including inputting a combination of these factors and the test results into a model that helps guide the physician in choosing a therapy and/or treatment regimen with that therapy.

IHC Assay Kits

In yet another embodiment of the invention, the reagents useful to perform immunohistochemistry on an FFPE tumor tissue section are provided in a kit along with instructions for performing the IHC assay and scoring PD-L1 expression on the tissue section in accordance with a scoring process described herein. The kit comprises a primary antibody, and may further comprise a secondary antibody. When the primary or secondary antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

Further embodiments also provide a processor, a computer readable memory, and a routine stored on the computer readable memory and adapted to be executed on the processor to perform any of the scoring processes described herein. Examples of suitable computing systems, environments, and/or configurations include personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, or any other systems known in the art.

EXEMPLARY SPECIFIC EMBODIMENTS OF THE INVENTION

1. A process for scoring the expression of a programmed death ligand 1 (PD-L1) protein in a tumor sample removed from an animal, comprising:
  (a) obtaining a tissue section from the tumor sample that has been stained in an immunohistochemical (IHC) assay with an antibody that specifically binds to the PD-L1 protein (anti-PD-L1 Ab);
  (b) examining each tumor nest in the tissue section for staining; and
  (c) assigning one or both of a modified H score (MHS) and a modified proportion score (MPS) to the tissue section,
  wherein assigning the MHS comprises (i) estimating, across all of the viable tumor cells and stained mononuclear inflammatory cells in all of the examined tumor nests, four separate percentages for cells that have no staining, weak staining (+1), moderate staining (+2) and strong staining (+3), wherein a cell must have at least partial membrane staining to be included in the weak, moderate or strong staining percentages, and wherein the sum of all four percentages equals 100; and (ii) inputting the estimated percentages into the formula of 1×(percent of weak staining cells)+2×(percent of moderate staining cells)+3×(percent of strong staining cells), and assigning the result of the formula to the tissue section as the MHS;
  wherein assigning the MPS comprises estimating, across all of the viable tumor cells and mononuclear inflammatory cells in all of the examined tumor nests, the percentage of cells that have at least partial membrane staining of any intensity, and assigning the resulting percentage to the tissue section as the MPS; and
  wherein if both the MHS and MPS are assigned, the assignments may be made in either order or simultaneously.

2. The process of embodiment 1, wherein the tumor sample is from a cancer selected from the group consisting of non-small cell lung carcinoma (NSCLC), head and neck squamous carcinoma, and transitional bladder carcinoma, and the process further comprises designating the tumor sample as positive or negative for PD-L1 expression, wherein
  the tumor sample is designated as positive for PD-L1 expression if either of the MHS or the MPS is greater than zero, and
  the tumor sample is designated as negative for PD-L1 expression if the MHS is zero or the MPS is zero.

3. The process of embodiment 2, wherein the cancer is NSCLC.

4. The process of any of the above embodiments, wherein only the MPS is assigned.

5. The process of embodiment 1 or 2, further comprising:
  examining the stroma surrounding each tumor nest for the presence or absence within the stroma of a band of membrane-stained cells, and
  assigning to the tissue section a stroma score of positive if the band is detected in the stroma surrounding at least one tumor nest, or
  assigning to the tissue section a stroma score of negative if the band is not detected in the tissue section.

6. The process of embodiment 5, wherein the tumor sample is from a cancer selected from the group consisting of non-small cell lung carcinoma (NSCLC), head and neck squamous carcinoma, and transitional bladder carcinoma, and the process further comprises designating the tumor sample as positive or negative for PD-L1 expression,
  wherein the tumor sample is designated as positive for PD-L1 expression if the tissue section has any one or more of the following score assignments:
    (i) the stroma score is positive,
    (ii) the MHS greater than zero, and
    (iii) the MPS is greater than zero, and
  wherein the tumor sample is designated as negative for PD-L1 expression if the tissue section has any one or more of the following score assignments:
    (iv) the stroma score is negative and the MHS is zero;
    (v) the stroma score is negative and the MPS is zero; and
    (vi) the stroma score is negative, the MHS is zero and the MPS is zero.

7. The process of embodiment 5, wherein the tumor sample is from a cancer selected from the group consisting of melanoma and breast cancer, and the process further comprises:
  examining each tumor nest for the presence or absence of a lattice pattern of membrane-stained dendriform cells within the tumor nest, and
  assigning to the tissue section a dendriform pattern score (DS) of positive if the lattice pattern is detected in at least one of the tumor nests, or
  assigning a DS of negative if the lattice pattern is not detected in any of the tumor nests.

8. The process of embodiment 7, further comprising designating the tumor sample as positive or negative for PD-L1 expression,
  wherein the tumor sample is designated as positive for PD-L1 expression if the tissue section has any one or more of the following score assignments:
    (i) the stroma score is positive,
    (ii) the DS is positive
    (iii) the MHS greater than zero, and
    (iv) the MPS is greater than zero; and
  wherein the tumor sample is designated as negative for PD-L1 expression if the tissue section has any one or more of the following score assignments:

(v) the stroma score is negative, the DS is negative and the MHS is zero;
(vi) the stroma score is negative, the DS is negative and the MPS is zero; and
(vi) the stroma score is negative, the DS is negative, the MHS is zero and the MPS is zero.

9. The process of any of the above embodiments, wherein the tumor sample is from a human and the PD-L1 protein is human PD-L1.

10. The process of embodiment 9, wherein the anti-PD-L1 Ab is selected from the group consisting of, the monoclonal antibody 20C3, the monoclonal antibody 22C3 or the monoclonal antibody 5H-1.

11. The process of embodiment 9, wherein the anti-PD-L1 Ab is the monoclonal antibody 22C3.

12. A method for predicting if a human patient diagnosed with non-small cell lung carcinoma (NSCLC) is likely to respond to treatment with a PD-1 antagonist, comprising:
    (a) obtaining a modified P score (MPS) for the level of expression of programmed death ligand 1 (PD-L1) in a tumor sample removed from the patient; wherein the MPS is obtained by performing a scoring process that comprises:
        (i) obtaining a tumor tissue section from the sample that has been stained in an immunohistochemical (IHC) assay with an antibody that specifically binds to human PD-L1 (anti-PD-L1 Ab);
        (ii) examining each tumor nest in the tissue section for staining; and
        (iii) assigning the modified P score (MPS) to the tissue section,
        wherein assigning the MPS comprises estimating, across all of the viable tumor cells and mononuclear inflammatory cells in all of the examined tumor nests, the percentage of cells that have at least partial membrane staining of any intensity; and
    (b) predicting the patient as likely to respond to the treatment if the MPS is at or above a specified threshold or predicting the patient as not likely to respond to the treatment if the MPS is below the specified threshold.

13. The method of embodiment 12, wherein the specified threshold is MPS=any number between 80 to 100.

14. The method of embodiment 13, wherein the specified threshold is MPS=any number between 85 to 95.

15. The method of embodiment 13, wherein the specified threshold is MPS=90.

16. The process or method of any of the above embodiments, wherein each of the estimated percentages used in calculating one of both of the MHS and the MPS is confined to a discrete estimate selected from the group consisting of 0, 1, 2, 5, 10, 15, 20, 30, 40, 50, 60, 70, 80, 85, 90, 95 and 100.

17. The process or method of any of the above embodiments, wherein the tumor tissue section is a formalin-fixed, paraffin-embedded tissue section.

18. The method of any of the above embodiments, wherein the anti-PD-L1 Ab is selected from the group consisting of, the monoclonal antibody 20C3, the monoclonal antibody 22C3 or the monoclonal antibody 5H-1.

19. The method of any of the above embodiments, wherein the anti-PD-L1 Ab is the monoclonal antibody 22C3.

20. The process or method of any of the above embodiments, wherein the tumor sample is from a human patient who is being evaluated for treatment with a PD-1 antagonist.

21. The process or method of embodiment 20, wherein the PD-1 antagonist is an anti-PD-1 monoclonal antibody that comprises a heavy chain and a light chain, and wherein the heavy chain comprises SEQ ID NO:32 and the light chain comprises SEQ ID NO:33.

22. The process or method of any of the above embodiments, wherein stained tumor cells that are outside of any tumor nests are included in the estimated percentages used in calculating the MHS and/or the MPS.

23. A method of treating a human patient diagnosed with non small cell lung carcinoma (NSCLC), the method comprising:
    (a) obtaining a diagnostic report that provides one or both of a modified H score (MHS) and a modified P score (MPS) for PD-L1 expression for a tumor sample removed from the patient; and
    (b) treating the patient with a PD-1 antagonist if one or both of the MHS and the MPS is at or above a specified threshold, or
    (c) treating the patient with a therapy that does not include a PD-1 antagonist if the MHS and the MPS are below the specified threshold,
    wherein the specified threshold is selected from the group consisting of: the MHS is greater than zero; the MPS is greater than zero; and the MHS and the MPS is greater than zero.
    wherein the MHS and the MPS were determined by a scoring process comprising:
        (i) staining a tissue section from the tumor sample in an immunohistochemical (IHC) assay with an antibody that specifically binds to human PD-L1 (anti-PD-L1 Ab);
        (ii) examining each tumor nest in the tissue section for staining; and
        (iii) assigning one or both of the MHS and MPS to the tissue section,
        wherein assigning the MHS comprises estimating, across all of the viable tumor cells and stained mononuclear inflammatory cells in all of the examined tumor nests, four separate percentages for cells that have no staining, weak staining, moderate staining and strong staining, wherein a cell must have at least partial membrane staining to be included in the weak, moderate or strong staining percentages, and wherein the sum of all four percentages equals 100; inputting the estimated percentages into the formula of MHS=1×(percent of weak staining cells)+2×(percent of moderate staining cells)+3×(percent of strong staining cells); and
        wherein assigning the MPS comprises estimating, across all of the viable tumor cells and mononuclear inflammatory cells in all of the examined tumor nests, the percentage of cells that have at least partial membrane staining of any intensity;
        wherein if both the MHS and MPS are assigned, the assignments may be performed in either order or simultaneously.

24. The method of embodiment 23, wherein the specified threshold is selected from the group consisting of (i) MHS=any number between 170 and 210, (ii) MPS=any number between 80 and 100; (iii) MHS=any number between 170 and 210, and MPS=any number between 80 and 100; (iv) MHS=any number between 185 and 195; and (v) MPS=any number between 85 and 95; (vi) MHS=190; (vii) MPS=90.

25. The method of any of embodiments 23 to 24, wherein the PD-1 antagonist is BMS-936558 (nivolumab), MPDL3280A, CT-011, ONO-4538, BMS-936559, MEDI4736 or AMP-224.

26. The method of any of embodiments 23 to 24, wherein the PD-1 antagonist is an anti-PD-1 antibody which comprises a heavy chain and a light chain, and wherein the heavy chain comprises SEQ ID NO:32 and the light chain comprises SEQ ID NO:33.

27. The method of any of embodiments 23 to 26, wherein the anti-PD-L1 antibody is the monoclonal antibody 22C3.

28. The method of any of embodiments 23 to 27, wherein only the MPS is assigned to the tissue section.

29. The process or method of any of the above embodiments, wherein the tissue section is from a patient who has been previously treated with ipilumumab.

EXAMPLES

Example 1. IHC Assay of FFPE Tissue Sections with the Monoclonal Antibody 22C3

Figure 2:
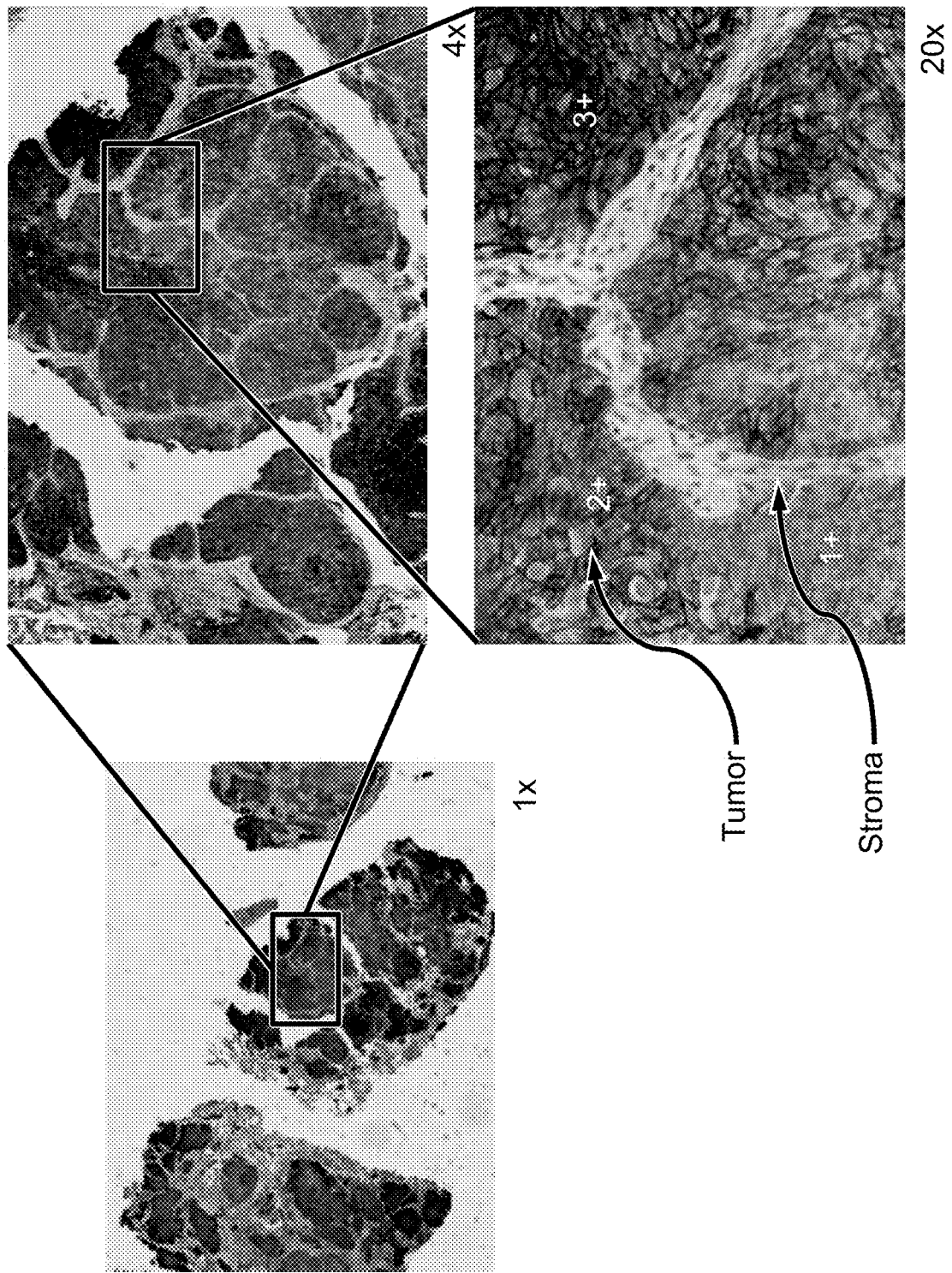
FIG. 2 shows images of an FFPE tissue section of NSCLC stained by IHC with the antibody 22C3, with the box indicating a particular field viewed at 1×, 4× and 20× magnification, the arrows indicating PD-L1 expressing tumor cells and PD-L1 negative stroma in this field at 20× magnification, with PD-L1 staining intensity scored as 1+ for weak staining, 2+ for moderate staining and 3+ for strong staining. A pathologist estimated the percentages of viable tumor cells and stained mononuclear inflammatory cells in the boxed field as being 30% weak staining, 20% moderate staining and 50% strong staining, and thus assigned the scores to the boxed field: MHS=220 (1×30%+2×20%+3×50%), MPS=100 and SS=negative.
Figure 3A:
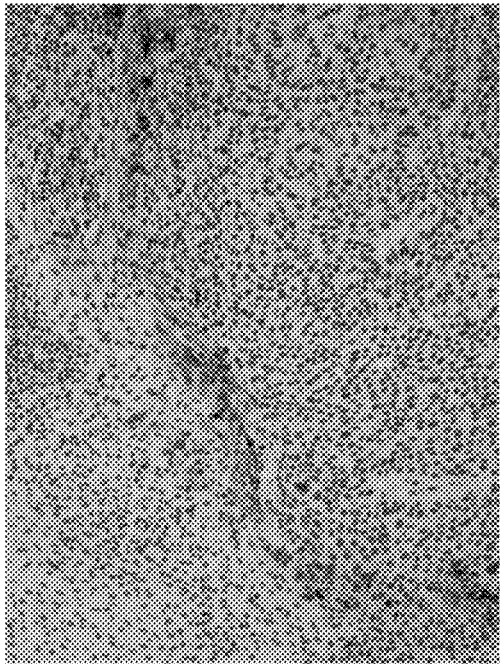
FIGS. 3A-3D show images of IHC staining by the antibody 22C3 in FFPE tissue sections of squamous cell carcinoma of the head and neck at 20× magnification, with FIG. 3A showing a field that has no PD-L1 staining in the stroma or tumor cells, FIG. 3B showing a field that has no PD-L1 staining in the tumor, but PD-L1 staining in the stroma, FIG. 3C showing a field that has moderate PD-L1 staining in the tumor with no staining of the stroma, and FIG. 3D showing strong staining of tumor with no staining of the stroma. The scoring process of the invention was used to assign the following scores to each displayed field: MHS=10, MPS=5 and SS=positive (FIG. 3A); MHS=0, MPS=0 and SS=positive (FIG. 3B); MHS=150, MPS=60 and SS=negative (FIG. 3C); and MHS=300, MPS=100 and SS=negative (FIG. 3D).
Figure 3B:
Figure 3C:
Figure 3D:
Figure 4C:
FIGS. 4A-4E show images of IHC staining by the antibody 22C3 in FFPE tissue sections of melanoma at 20× magnification, with FIG. 4A showing a field that has staining of melanin, but no PD-L1 membrane staining, FIGS. 4B and 4C showing fields that have PD-L1 membrane staining in the tumor, FIG. 4D showing a field that has PD-L1 staining in the stroma and the tumor, and FIG. 4E showing a dendriform pattern of PD-L1 staining. The scoring process of the invention was used to assign the following scores to each displayed field: MHS=0, MPS=0, SS=negative, DS=negative (FIG. 4A); MHS=220, MPS=100, SS=negative and DS=negative (FIG. 4B); MHS=240, MPS=80, SS=negative and DS=negative.
Figure 4B:
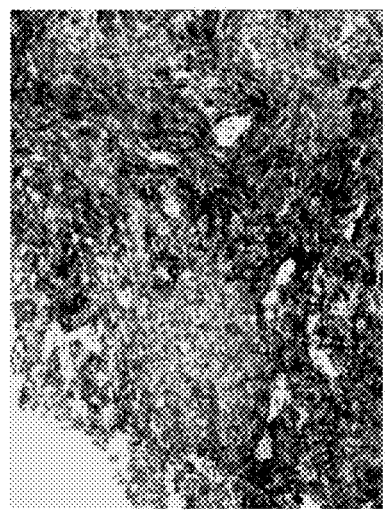
Figure 4A:
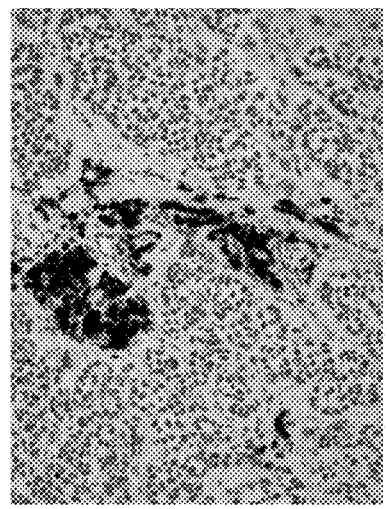
Figure 4E:
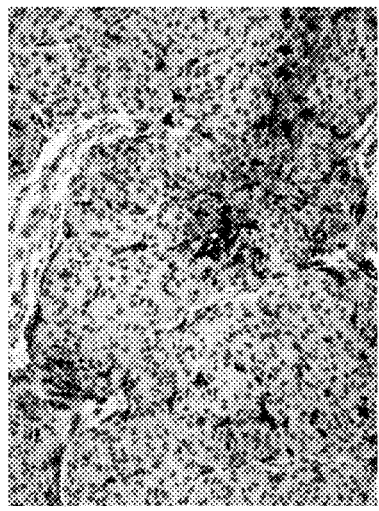
Figure 4D:
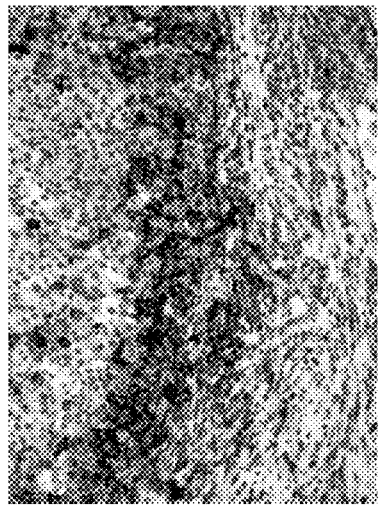
Figure 5B:
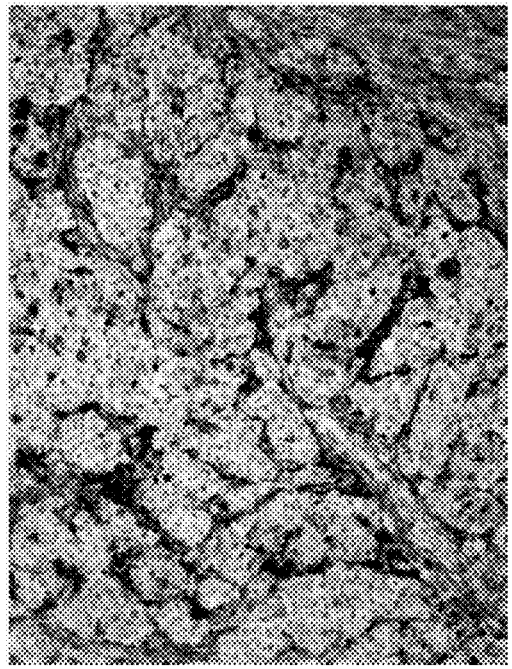
FIGS. 5A-5C show images of IHC staining by the antibody 22C3 in FFPE tissue sections of breast cancer at 20× magnification, with FIG. 5A showing a field that has a stained dendriform pattern, FIG. 5B showing a field that has stromal PD-L1 staining within the smaller intercalating regions.
Figure 5C:
Figure 5A:
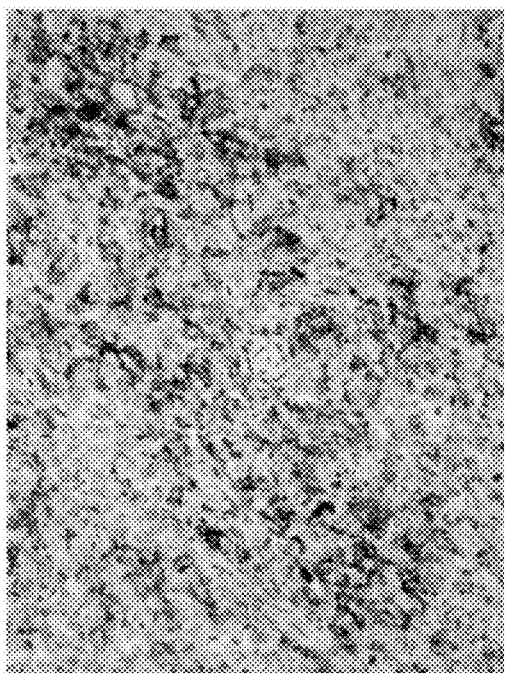
Figure 6A:
FIGS. 6A-6C show images of IHC staining by the antibody 22C3 in FFPE tissue sections of transitional cell carcinoma of the bladder at 40× magnification, with FIG. 6A showing a field that has no PD-L1 staining, and FIGS. 6B and 6C showing a field that has PD-L1 staining in the tumor. The scoring process of the invention was used to assign the following scores to each displayed field: MHS=0, MPS=0, SS=negative (FIG. 6A); MHS=180, MPS=100, SS=negative (FIG. 6B); and MHS=130, MPS=40, and SS=negative (FIG. 6C).
Figure 6B:
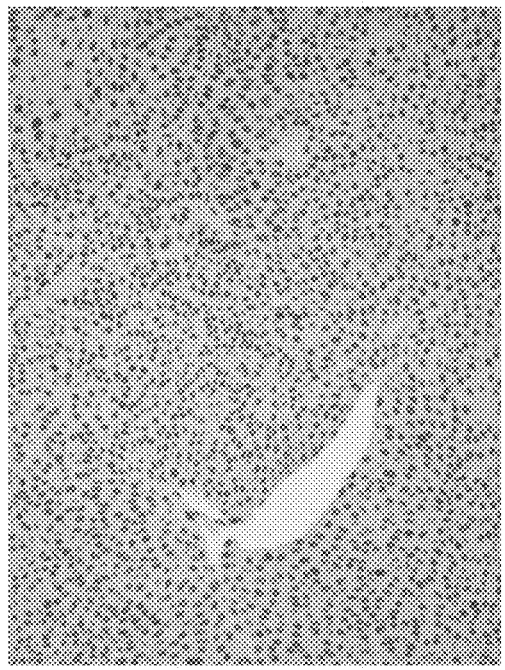
Figure 6C:
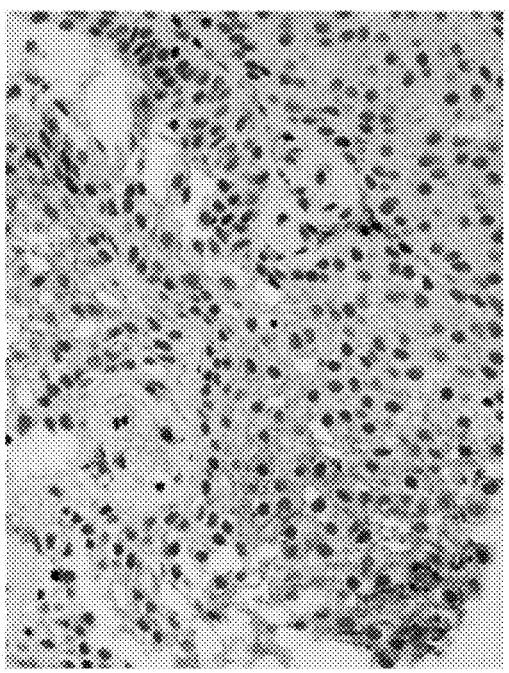

This Example describes the IHC assay used for the stained tumor tissue sections shown in FIGS. 1-6.

Step 1 Slide Preparation:
a. Four-micron (4 μm) sections are mounted onto Fisher Biotech 22-230-900 ProbeOn Plus microscope slides or other positively charged glass slide.
b. Slides are baked for 45 min at 60° C. (dry-heat), no later than 24 hrs prior to initiation of Step 2, or a minimum of 15 min at room temperature prior to initiation of Step 2

Step 2 Dewax/Pre-Antigen Retrieval/Unmasking:
a. Four (4) changes of room temperature (25° C.) absolute xylene for 5 min each with no agitation;
b. Two (2) changes of room temperature (25° C.) absolute alcohol for 2 min each with no agitation;
c. Two (2) changes of room temperature (25° C.) 70% alcohol for 2 min each with no agitation;
d. Two (2) changes of room temperature (25° C.) 30% alcohol for 2 min each with no agitation;
e. Two (2) changes of room temperature (25° C.) distilled water for rinsing using a minimum of 16 dips in-out; and
f. Slides are immersed in room temperature (25° C.) distilled water and then transferred to antigen/epitope retrieval/unmasking platform.

Step 3 Antigen/Epitope Retrieval/Unmasking with Steamer:
a. Commercial steamer pre-heated to 97° C.
b. Heat induced antigen/epitope retrieval/unmasking using 1×DAKO S1699 low pH Target Retrieval Solution, 97° C. for 20 min. Ten (10) tissue sections are face-paired with clean blank slides in TechMate reagent trays containing exactly 10 mL antigen/epitope retrieval/unmasking solution to capillary draw reagent up and over the tissues. Tissue sections on slides are bathed in antigen/epitope retrieval/unmasking solution in presence of steam heat.
c. Post-antigen/epitope retrieval/unmasking cool for 5 min, slide pairs firmly inserted into a TechMate slide holder and drained of DAKO S1699 low pH Target Retrieval Solution with an absorbent wick pad.
d. Wash two (2) times manually using capillary action (drain-draw) with FLEX+ wash buffer (part of DAKO K8012 EnVision FLEX+ kit [no more than 1wk diluted from 20× concentrate]).

Step 4 Immunohistochemistry:
EnVision FLEX+ reagents are stored at 2-8° C., dispense or dilute as necessary, with all procedures below automated at room temperature (25° C.). Reagent changes (washes, incubations) take place by capillary action (drain-draw) using absorbent wick pads (drain) and TechMate reagent trays (draw).

a. Wash three (3) times with FLEX+ wash buffer (part of DAKO K8012 [no more than 1wk diluted from 20× concentrate])
b. DAKO 53020 Proteinase K diluted 1/160 in FLEX+ wash buffer, 10 mins
c. Wash three (3) times with FLEX+ wash buffer
d. ENVision FLEX+ Peroxidase Block (part of DAKO K8012), 2×5 min (10 min total) with intervening reagent drain
e. Wash two (2) times with FLEX+ wash buffer
f. PD-L1 22C3 antibody, freshly diluted in DAKO S0809 Primary Antibody Diluent from 0.1 mg/mL antibody working stock (also in DAKO S0809), 2 micrograms/mL for 16 hrs. Overnight incubation is off-platform in a dark humidified chamber, i.e., slides are physically 'removed' from TechMate platform, though are held firm by the TechMate slide holder in TechMate reagent trays containing primary antibody
g. Wash five (5) times with FLEX+ wash buffer
h. ENVision FLEX+ Mouse Linker (part of DAKO K8012), 15 min
i. Wash four (4) times with FLEX+ wash buffer
j. ENVision FLEX+ HRP-polymer (part of DAKO K8012), 20 min
k. Wash five (5) times with FLEX+ wash buffer
l. ENVision FLEX+ DAB+ Chromogen (part of DAKO K8012 [light-sensitive reagent made freshly made at conclusion of primary antibody incubation, using 1 drop FLEX+ DAB chromogen concentrate per 1 mL FLEX+ substrate buffer]), 2×5 min (10 min total) with intervening reagent drain and one (1) wash in FLEX+ wash buffer
m. Wash four (4) times with FLEX+ wash buffer
n. DAKO S1961 DAB Enhancer, 2×5 min with intervening reagent drain and one (1) wash in FLEX+ wash buffer (10 min total)
o. Wash four (4) times with FLEX+ wash buffer
p. Counterstain with DAKO 53301 hematoxylin, 1 min
q. Wash six (6) times with FLEX+ wash buffer
r. Slides immersed in room temperature (25° C.) distilled water (transfer to coverslip area)

Step 5 Dehydration/Pre-Coverslipping:
a. Two (2) changes of room temperature (25° C.) 95% alcohol for rinsing with minimum of 16 dips in-out
b. Six (6) changes of room temperature (25° C.) absolute alcohol for rinsing with minimum of 16 dips in-out
c. Four (4) changes of room temperature (25° C.) absolute xylene for rinsing minimum of 16 dips in-out
d. Coverslip with Thermo Scientific 8312 Cytoseal XYL non-aqueous semi-permanent mounting media Immunohistochemical applications may be manually operated or automated. Automated systems can perform all the staining steps as described above. Laboratory equipment necessary to perform the assay include a heat source (steamer) and automated staining platform (such as TechMate).

Example 2. Scoring of FFPE Tissue Sections from Different Cancer Types for PD-L1 Expression FIGS. 1 to 6 illustrate how FFPE tissue sections stained with an anti-PD-L1 antibody in the IHC assay described in Example 1 would be scored for PD-L1 expression using the scoring process of the present invention. The Brief Description of the Figures lists the various scores that were assigned to individual fields of each tissue section for illustrative purposes only. However, a scoring process of the invention is to be performed by examining the entire tissue section on the slide, and in practice, the pathologist would score a slide for PD-L1 expression by viewing the tissue section on the slide at low, medium and high magnification.

Example 3. Response of Non-Small Cell Lung Cancer is Correlated with the Level of PD-L1 Expression The scoring process described above was used to score PD-L1 expression in tissue sections of NSCLC tumor samples removed from patients prior to treatment with an anti-PD-1 antibody, which comprised the heavy and light chains set forth in SEQ ID NOs: 33 and 32, respectively. When the PD-L1 expression score was correlated with tumor response, the results indicated that higher MHS and MPS values predict tumor response, irrespective of stroma score, and also that the MPS was as predictive as the MHS in predicting tumor response in this patient group. The following table summarizes the results of these correlations.

| PDL-1 Score | Number of Patients | |
| --- | --- | --- |
| | No tumor Response | Tumor Response |
| MHS ≤ 180 | 21 | 1 |
| MHS ≥ 200 | 2 | 6 |
| MPS < 90 | 21 | 1 |
| MPS > 90 | 2 | 6 |

All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

The foregoing written specification is considered to be sufficient to enable one skilled in the art to practice the invention. Various modifications of the invention in addition to those shown and described herein will become apparent to those skilled in the art from the foregoing description and fall within the scope of the appended claims.

The invention claimed is:

1. A method for treating a human patient diagnosed with non small cell lung carcinoma (NSCLC), the method comprising:
    a. obtaining a diagnostic report that provides one or both of a modified H score (MHS) and a modified P score (MPS) for PD-L1 expression for a tumor sample removed from the patient,
    wherein a specified threshold is selected from the group consisting of: (i) MHS=190; (ii) MPS=90; and (iii) MHS=190 and MPS=90;
    wherein the MHS and the MPS were determined by a scoring process comprising:
        (i) staining a tissue section from the tumor sample in an immunohistochemical (IHC) assay with an antibody that specifically binds to human PD-L1 (anti-PD-L1 Ab), wherein the anti-PD-L1 antibody is a monoclonal antibody which comprises a light chain mature variable region of SEQ ID NO:6 and a heavy chain mature variable region of SEQ ID NO:14, or the anti-PD-L1 antibody is a monoclonal antibody which comprises a light chain mature variable region of SEQ ID NO:21 and a heavy chain mature variable region of SEQ ID NO:29;
        (ii) examining each tumor nest in the tissue section for staining; and
        (iii) assigning one or both of the MHS and MPS to the tissue section,
    wherein assigning the MHS comprises estimating, across all of the viable tumor cells and stained mononuclear inflammatory cells in all of the examined tumor nests, four separate percentages for cells that have no staining, weak staining, moderate staining and strong staining, wherein a cell must have at least partial membrane staining to be included in the weak, moderate or strong staining percentages, and wherein the sum of all four percentages equals 100; inputting the estimated percentages into the formula of MHS=1x(percent of weak staining cells)+2x(percent of moderate staining cells)+3x(percent of strong staining cells);
    wherein assigning the MPS comprises estimating, across all of the viable tumor cells and mononuclear inflammatory cells in all of the examined tumor nests, the percentage of cells that have at least partial membrane staining of any intensity; and
    wherein if both the MHS and MPS are assigned, the assignments may be performed in either order or simultaneously; and
    b. administering a PD-1 antagonist to the patient if one or both of the MHS and the MPS is at or above the specified threshold.

2. The method of claim 1, wherein the PD-1 antagonist is BMS-936558 (nivolumab), MPDL3280A, CT-011, ONO-4538, BMS-936559, MEDI4736, AMP-224 or an anti-PD-1 antibody which comprises a heavy chain and a light chain, and wherein the heavy chain comprises SEQ ID NO:32 and the light chain comprises SEQ ID NO:33.

3. The method of claim 2, wherein the PD-1 antagonist is BMS-936558 (nivolumab).

4. The method of claim 2, wherein the PD-1 antagonist is an anti-PD-1 antibody which comprises a heavy chain and a light chain, and wherein the heavy chain comprises SEQ ID NO:32 and the light chain comprises SEQ ID NO:33.

* * * * *

UNITED STATES PATENT AND TRADEMARK OFFICE
CERTIFICATE OF CORRECTION

| | | |
|---|---|---|
| PATENT NO. | : 11,193,937 B2 | Page 1 of 1 |
| APPLICATION NO. | : 15/712246 | |
| DATED | : December 7, 2021 | |
| INVENTOR(S) | : Dolled-Filhart et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 5 days.

Signed and Sealed this
Tenth Day of January, 2023

Katherine Kelly Vidal
*Director of the United States Patent and Trademark Office*

SEQUENCE LISTING

```
<160> NUMBER OF SEQ ID NOS: 33

<210> SEQ ID NO 1
<211> LENGTH: 17
<212> TYPE: PRT
<213> ORGANISM: Mus musculus

<400> SEQUENCE: 1

Lys Ser Ser Gln Ser Leu Leu Asn Ser Arg Thr Arg Lys Asn Tyr Leu
1               5                   10                  15

Ala

<210> SEQ ID NO 2
<211> LENGTH: 7
<212> TYPE: PRT
<213> ORGANISM: Mus musculus

<400> SEQUENCE: 2

Trp Ala Ser Thr Arg Glu Ser
1               5

<210> SEQ ID NO 3
<211> LENGTH: 8
<212> TYPE: PRT
<213> ORGANISM: Mus musculus

<400> SEQUENCE: 3

Gln Gln Ser Tyr Asp Val Val Thr
1               5
```

```
<210> SEQ ID NO 4
<211> LENGTH: 20
<212> TYPE: PRT
<213> ORGANISM: Mus musculus

<400> SEQUENCE: 4

Met Asp Ser Gln Ala Gln Val Leu Ile Leu Leu Leu Trp Val Ser
1               5                   10                  15

Gly Thr Phe Gly
            20

<210> SEQ ID NO 5
<211> LENGTH: 132
<212> TYPE: PRT
<213> ORGANISM: Mus musculus

<400> SEQUENCE: 5

Met Asp Ser Gln Ala Gln Val Leu Ile Leu Leu Leu Trp Val Ser
1               5                   10                  15

Gly Thr Phe Gly Asp Ile Val Met Ser Gln Ser Pro Ser Ser Leu Ala
            20                  25                  30

Val Ser Ala Gly Glu Lys Val Thr Met Ser Cys Lys Ser Ser Gln Ser
        35                  40                  45

Leu Leu Asn Ser Arg Thr Arg Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys Gln Gln Ser Tyr Asp Val Val Thr Phe Gly Ala Gly Thr Lys
        115                 120                 125

Leu Glu Leu Lys
    130

<210> SEQ ID NO 6
<211> LENGTH: 112
<212> TYPE: PRT
<213> ORGANISM: Mus musculus

<400> SEQUENCE: 6

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Gln
                85                  90                  95

Ser Tyr Asp Val Val Thr Phe Gly Ala Gly Thr Lys Leu Glu Leu Lys
            100                 105                 110
```

-continued

```
<210> SEQ ID NO 7
<211> LENGTH: 396
<212> TYPE: DNA
<213> ORGANISM: Mus musculus

<400> SEQUENCE: 7
atggattcac aggcccaggt tcttatattg ctgctgctat gggtatctgg tacctttggg      60
gacattgtga tgtcacaatc tccatcctcc ctggctgtgt cagcaggaga gaaggtcact     120
atgagctgca atccagtca gagtctgctc aacagtagaa cccgaaagaa ctacttggct     180
tggtaccagc agaaaccagg gcagtctcct aaactgctga tctactgggc atccactagg    240
gaatctgggg tccctgatcg cttcacaggc agtggatctg ggacagattt cactctcacc    300
atcagcagtg tgcaggctga agacctggca gtttattact gccagcaatc ttatgatgtg    360
gtcacgttcg gtgctgggac caagctggag ctgaaa                              396

<210> SEQ ID NO 8
<211> LENGTH: 5
<212> TYPE: PRT
<213> ORGANISM: Mus musculus

<400> SEQUENCE: 8

Ser Tyr Trp Met His
1               5

<210> SEQ ID NO 9
<211> LENGTH: 10
<212> TYPE: PRT
<213> ORGANISM: Mus musculus

<400> SEQUENCE: 9

Gly Tyr Ile Phe Thr Ser Tyr Trp Met His
1               5                   10

<210> SEQ ID NO 10
<211> LENGTH: 17
<212> TYPE: PRT
<213> ORGANISM: Mus musculus

<400> SEQUENCE: 10

Tyr Ile Asn Pro Ser Ser Asp Tyr Asn Glu Tyr Ser Glu Lys Phe Met
1               5                   10                  15

Asp

<210> SEQ ID NO 11
<211> LENGTH: 13
<212> TYPE: PRT
<213> ORGANISM: Mus musculus

<400> SEQUENCE: 11

Ser Gly Trp Leu Val His Gly Asp Tyr Tyr Phe Asp Tyr
1               5                   10

<210> SEQ ID NO 12
<211> LENGTH: 19
<212> TYPE: PRT
<213> ORGANISM: Mus musculus

<400> SEQUENCE: 12

Met Glu Arg His Trp Ile Phe Leu Phe Leu Phe Ser Val Thr Ala Gly
1               5                   10                  15

Val His Ser
```

-continued

```
<210> SEQ ID NO 13
<211> LENGTH: 141
<212> TYPE: PRT
<213> ORGANISM: Mus musculus

<400> SEQUENCE: 13

Met Glu Arg His Trp Ile Phe Leu Phe Leu Phe Ser Val Thr Ala Gly
1               5                   10                  15

Val His Ser Gln Val Gln Val Gln Ser Gly Ala Glu Leu Ala Glu
            20                  25                  30

Pro Gly Ala Ser Val Lys Met Ser Cys Lys Ala Ser Gly Tyr Ile Phe
        35                  40                  45

Thr Ser Tyr Trp Met His Trp Leu Lys Gln Arg Pro Gly Gln Gly Leu
    50                  55                  60

Glu Trp Ile Gly Tyr Ile Asn Pro Ser Ser Asp Tyr Asn Glu Tyr Ser
65                  70                  75                  80

Glu Lys Phe Met Asp Lys Ala Thr Leu Thr Ala Asp Lys Ala Ser Thr
                85                  90                  95

Thr Ala Tyr Met Gln Leu Ile Ser Leu Thr Ser Glu Asp Ser Ala Val
            100                 105                 110

Tyr Tyr Cys Ala Arg Ser Gly Trp Leu Val His Gly Asp Tyr Tyr Phe
        115                 120                 125

Asp Tyr Trp Gly Gln Gly Thr Thr Leu Thr Val Ser Ser
    130                 135                 140

<210> SEQ ID NO 14
<211> LENGTH: 122
<212> TYPE: PRT
<213> ORGANISM: Mus musculus

<400> SEQUENCE: 14

Gln Val Gln Val Gln Ser Gly Ala Glu Leu Ala Glu Pro Gly Ala
1               5                   10                  15

Ser Val Lys Met Ser Cys Lys Ala Ser Gly Tyr Ile Phe Thr Ser Tyr
            20                  25                  30

Trp Met His Trp Leu Lys Gln Arg Pro Gly Gln Gly Leu Glu Trp Ile
        35                  40                  45

Gly Tyr Ile Asn Pro Ser Ser Asp Tyr Asn Glu Tyr Ser Glu Lys Phe
    50                  55                  60

Met Asp Lys Ala Thr Leu Thr Ala Asp Lys Ala Ser Thr Thr Ala Tyr
65                  70                  75                  80

Met Gln Leu Ile Ser Leu Thr Ser Glu Asp Ser Ala Val Tyr Tyr Cys
                85                  90                  95

Ala Arg Ser Gly Trp Leu Val His Gly Asp Tyr Tyr Phe Asp Tyr Trp
            100                 105                 110

Gly Gln Gly Thr Thr Leu Thr Val Ser Ser
        115                 120

<210> SEQ ID NO 15
<211> LENGTH: 423
<212> TYPE: DNA
<213> ORGANISM: Mus musculus

<400> SEQUENCE: 15
atggaaaggc actggatctt tctcttcctg ttttcagtaa ctgcaggtgt ccactcccag    60
gtccaggttc agcagtctgg ggctgaactg gcagaacctg gggcctcagt gaagatgtcc   120
tgcaaggcct ctggctacat ctttactagc tactggatgc actggctaaa gcagaggcct   180
```

```
ggacagggtc tggaatggat tggatacatt aatcccagca gtgattataa tgaatacagt    240
gagaaattca tggacaaggc cacattgact gcagacaaag cctccaccac agcctacatg    300
caactgatca gcctgacatc tgaggactct gcagtctatt actgtgcaag atcgggatgg    360
ttagtacatg gagactatta ttttgactac tggggccaag gcaccactct cacagtctcc    420
tca                                                                 423
```

```
<210> SEQ ID NO 16
<211> LENGTH: 17
<212> TYPE: PRT
<213> ORGANISM: Mus musculus

<400> SEQUENCE: 16

Lys Ser Ser Gln Ser Leu Leu His Thr Ser Thr Arg Lys Asn Tyr Leu
1               5                   10                  15
Ala

<210> SEQ ID NO 17
<211> LENGTH: 7
<212> TYPE: PRT
<213> ORGANISM: Mus musculus

<400> SEQUENCE: 17

Trp Ala Ser Thr Arg Glu Ser
1               5

<210> SEQ ID NO 18
<211> LENGTH: 8
<212> TYPE: PRT
<213> ORGANISM: Mus musculus

<400> SEQUENCE: 18

Lys Gln Ser Tyr Asp Val Val Thr
1               5

<210> SEQ ID NO 19
<211> LENGTH: 20
<212> TYPE: PRT
<213> ORGANISM: Mus musculus

<400> SEQUENCE: 19

Met Asp Ser Gln Ala Gln Val Leu Ile Leu Leu Leu Leu Trp Val Ser
1               5                   10                  15
Gly Thr Cys Gly
            20

<210> SEQ ID NO 20
<211> LENGTH: 132
<212> TYPE: PRT
<213> ORGANISM: Mus musculus

<400> SEQUENCE: 20

Met Asp Ser Gln Ala Gln Val Leu Ile Leu Leu Leu Leu Trp Val Ser
1               5                   10                  15

Gly Thr Cys Gly Asp Ile Val Met Ser Gln Ser Pro Ser Ser Leu Ala
            20                  25                  30

Val Ser Ala Gly Glu Lys Val Thr Met Thr Cys Lys Ser Ser Gln Ser
        35                  40                  45

Leu Leu His Thr Ser Thr Arg Lys Asn Tyr Leu Ala Trp Tyr Gln Gln
    50                  55                  60
```

```
Lys Pro Gly Gln Ser Pro Lys Leu Leu Ile Tyr Trp Ala Ser Thr Arg
 65                  70                  75                  80

Glu Ser Gly Val Pro Asp Arg Phe Thr Gly Ser Gly Ser Gly Thr Asp
                 85                  90                  95

Phe Thr Leu Thr Ile Ser Ser Val Gln Ala Glu Asp Leu Ala Val Tyr
            100                 105                 110

Tyr Cys Lys Gln Ser Tyr Asp Val Val Thr Phe Gly Ala Gly Thr Lys
        115                 120                 125

Leu Glu Leu Lys
    130

<210> SEQ ID NO 21
<211> LENGTH: 112
<212> TYPE: PRT
<213> ORGANISM: Mus musculus

<400> SEQUENCE: 21

Asp Ile Val Met Ser Gln Ser Pro Ser Ser Leu Ala Val Ser Ala Gly
 1               5                  10                  15

Glu Lys Val Thr Met Thr Cys Lys Ser Ser Gln Ser Leu Leu His Thr
             20                  25                  30

Ser Thr Arg Lys Asn Tyr Leu Ala Trp Tyr Gln Gln Lys Pro Gly Gln
         35                  40                  45

Ser Pro Lys Leu Leu Ile Tyr Trp Ala Ser Thr Arg Glu Ser Gly Val
     50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Lys Gln
                 85                  90                  95

Ser Tyr Asp Val Val Thr Phe Gly Ala Gly Thr Lys Leu Glu Leu Lys
            100                 105                 110

<210> SEQ ID NO 22
<211> LENGTH: 396
<212> TYPE: DNA
<213> ORGANISM: Mus musculus

<400> SEQUENCE: 22
atggattcac aggcccaggt tcttatattg ctgctgctat gggtatctgg tacctgtggg    60
gacattgtga tgtcacagtc tccctcctcc ctggctgtgt cagcaggaga gaaggtcact   120
atgacctgca aatccagtca gagtctgctc cacactagca cccgaaagaa ctacttggct   180
tggtaccagc agaaaccagg gcagtctcct aaactgctga tctattgggc atccactagg   240
gaatctgggg tccctgatcg cttcacaggc agtggatctg ggacagattt cactctcacc   300
atcagcagtg tgcaggctga agacctggca gtttattact gcaaacaatc ttatgatgtg   360
gtcacgttcg gtgctgggac caagctggag ctgaaa                             396

<210> SEQ ID NO 23
<211> LENGTH: 5
<212> TYPE: PRT
<213> ORGANISM: Mus musculus

<400> SEQUENCE: 23

Ser Tyr Trp Ile His
 1               5
```

```
<210> SEQ ID NO 24
<211> LENGTH: 10
<212> TYPE: PRT
<213> ORGANISM: Mus musculus

<400> SEQUENCE: 24

Gly Thr Thr Phe Thr Ser Tyr Trp Ile His
1               5                   10

<210> SEQ ID NO 25
<211> LENGTH: 17
<212> TYPE: PRT
<213> ORGANISM: Mus musculus

<400> SEQUENCE: 25

Tyr Ile Asn Pro Ser Ser Gly Tyr His Glu Tyr Asn Gln Lys Phe Ile
1               5                   10                  15

Asp

<210> SEQ ID NO 26
<211> LENGTH: 13
<212> TYPE: PRT
<213> ORGANISM: Mus musculus

<400> SEQUENCE: 26

Ser Gly Trp Leu Ile His Gly Asp Tyr Tyr Phe Asp Phe
1               5                   10

<210> SEQ ID NO 27
<211> LENGTH: 19
<212> TYPE: PRT
<213> ORGANISM: Mus musculus

<400> SEQUENCE: 27

Met Glu Arg His Trp Ile Phe Leu Phe Leu Phe Ser Val Thr Ala Gly
1               5                   10                  15

Val His Ser

<210> SEQ ID NO 28
<211> LENGTH: 141
<212> TYPE: PRT
<213> ORGANISM: Mus musculus

<400> SEQUENCE: 28

Met Glu Arg His Trp Ile Phe Leu Phe Leu Phe Ser Val Thr Ala Gly
1               5                   10                  15

Val His Ser Gln Val His Leu Gln Gln Ser Gly Ala Glu Leu Ala Lys
            20                  25                  30

Pro Gly Ala Ser Val Lys Met Ser Cys Lys Ala Ser Gly Tyr Thr Phe
        35                  40                  45

Thr Ser Tyr Trp Ile His Trp Ile Lys Gln Arg Pro Gly Gln Gly Leu
    50                  55                  60

Glu Trp Ile Gly Tyr Ile Asn Pro Ser Ser Gly Tyr His Glu Tyr Asn
65                  70                  75                  80

Gln Lys Phe Ile Asp Lys Ala Thr Leu Thr Ala Asp Arg Ser Ser Ser
                85                  90                  95

Thr Ala Tyr Met His Leu Thr Ser Leu Thr Ser Glu Asp Ser Ala Val
            100                 105                 110
```

```
Tyr Tyr Cys Ala Arg Ser Gly Trp Leu Ile His Gly Asp Tyr Tyr Phe
            115                 120                 125

Asp Phe Trp Gly Gln Gly Thr Thr Leu Thr Val Ser Ser
    130                 135                 140

<210> SEQ ID NO 29
<211> LENGTH: 122
<212> TYPE: PRT
<213> ORGANISM: Mus musculus

<400> SEQUENCE: 29

Gln Val His Leu Gln Gln Ser Gly Ala Glu Leu Ala Lys Pro Gly Ala
1               5                   10                  15

Ser Val Lys Met Ser Cys Lys Ala Ser Gly Tyr Thr Phe Thr Ser Tyr
            20                  25                  30

Trp Ile His Trp Ile Lys Gln Arg Pro Gly Gln Gly Leu Glu Trp Ile
        35                  40                  45

Gly Tyr Ile Asn Pro Ser Ser Gly Tyr His Glu Tyr Asn Gln Lys Phe
    50                  55                  60

Ile Asp Lys Ala Thr Leu Thr Ala Asp Arg Ser Ser Ser Thr Ala Tyr
65                  70                  75                  80

Met His Leu Thr Ser Leu Thr Ser Glu Asp Ser Ala Val Tyr Tyr Cys
                85                  90                  95

Ala Arg Ser Gly Trp Leu Ile His Gly Asp Tyr Tyr Phe Asp Phe Trp
            100                 105                 110

Gly Gln Gly Thr Thr Leu Thr Val Ser Ser
        115                 120

<210> SEQ ID NO 30
<211> LENGTH: 423
<212> TYPE: DNA
<213> ORGANISM: Mus musculus

<400> SEQUENCE: 30
atggaaaggc actggatctt tctcttcctg ttttcagtaa ctgcaggtgt ccactcccag      60
gtccaccttc agcagtctgg ggctgaactg gcaaaacctg gggcctcagt gaagatgtcc     120
tgcaaggctt ctggctacac gtttactagt tactggatac actggataaa gcagaggcct     180
ggacagggtc tggaatggat tggatacatt aatccttcct ctggttatca tgaatacaat     240
cagaaattca ttgacaaggc cacattgact gctgacagat cctccagcac agcctacatg     300
cacctgacca gcctgacgtc tgaagactct gcagtctatt actgtgcaag atcgggatgg     360
ttaatacatg gagactacta ctttgacttc tggggccaag gcaccactct cacagtctcc     420
tca                                                                   423

<210> SEQ ID NO 31
<211> LENGTH: 290
<212> TYPE: PRT
<213> ORGANISM: Homo sapiens

<400> SEQUENCE: 31

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45
```

```
Asp Leu Ala Ala Leu Ile Val Tyr Trp Glu Met Glu Asp Lys Asn Ile
 50                  55                  60

Ile Gln Phe Val His Gly Glu Glu Asp Leu Lys Val Gln His Ser Ser
 65                  70                  75                  80

Tyr Arg Gln Arg Ala Arg Leu Leu Lys Asp Gln Leu Ser Leu Gly Asn
                 85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290

<210> SEQ ID NO 32
<211> LENGTH: 447
<212> TYPE: PRT
<213> ORGANISM: Artificial Sequence
<220> FEATURE:
<223> OTHER INFORMATION: Light chain of humanized antibody

<400> SEQUENCE: 32

Gln Val Gln Leu Val Gln Ser Gly Val Glu Val Lys Lys Pro Gly Ala
 1               5                  10                  15

Ser Val Lys Val Ser Cys Lys Ala Ser Gly Tyr Thr Phe Thr Asn Tyr
                20                  25                  30

Tyr Met Tyr Trp Val Arg Gln Ala Pro Gly Gln Gly Leu Glu Trp Met
            35                  40                  45

Gly Gly Ile Asn Pro Ser Asn Gly Gly Thr Asn Phe Asn Glu Lys Phe
 50                  55                  60

Lys Asn Arg Val Thr Leu Thr Thr Asp Ser Ser Thr Thr Thr Ala Tyr
 65                  70                  75                  80

Met Glu Leu Lys Ser Leu Gln Phe Asp Asp Thr Ala Val Tyr Tyr Cys
                 85                  90                  95

Ala Arg Arg Asp Tyr Arg Phe Asp Met Gly Phe Asp Tyr Trp Gly Gln
            100                 105                 110
```

```
Gly Thr Thr Val Thr Val Ser Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 33
<211> LENGTH: 218
<212> TYPE: PRT
<213> ORGANISM: Artificial Sequence
<220> FEATURE:
<223> OTHER INFORMATION: Light chain of humanized antibody

<400> SEQUENCE: 33

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30
```

-continued

```
Gly Tyr Ser Tyr Leu His Trp Tyr Gln Gln Lys Pro Gly Gln Ala Pro
         35                  40                  45

Arg Leu Leu Ile Tyr Leu Ala Ser Tyr Leu Glu Ser Gly Val Pro Ala
 50                      55                  60

Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Tyr Cys Gln His Ser Arg
             85                  90                  95

Asp Leu Pro Leu Thr Phe Gly Gly Gly Thr Lys Val Glu Ile Lys Arg
             100                 105                 110

Thr Val Ala Ala Pro Ser Val Phe Ile Phe Pro Pro Ser Asp Glu Gln
             115                 120                 125

Leu Lys Ser Gly Thr Ala Ser Val Val Cys Leu Leu Asn Asn Phe Tyr
             130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
             165                 170                 175

Tyr Ser Leu Ser Ser Thr Leu Thr Leu Ser Lys Ala Asp Tyr Glu Lys
             180                 185                 190

His Lys Val Tyr Ala Cys Glu Val Thr His Gln Gly Leu Ser Ser Pro
             195                 200                 205

Val Thr Lys Ser Phe Asn Arg Gly Glu Cys
             210                 215
```